US006451853B1

(12) United States Patent
Taub et al.

(10) Patent No.: US 6,451,853 B1
(45) Date of Patent: Sep. 17, 2002

(54) SMALL MOLECULES THAT ELICIT A POLARIZED TH1 RESPONSE AND FOR MODULATION OF CELLULAR IMMUNITY

(75) Inventors: Floyd E. Taub; Carol H. Pontzer, both of Silver Spring, MD (US)

(73) Assignee: Dovetail Technologies, Inc, College Park, MD (US)

(*) Notice: Subject to any disclaimer, the term of this patent is extended or adjusted under 35 U.S.C. 154(b) by 0 days.

(21) Appl. No.: 09/256,762

(22) Filed: Feb. 24, 1999

Related U.S. Application Data (60) Provisional application No. 60/075,966, filed on Feb. 24, 1998, and provisional application No. 60/085,474, filed on May 14, 1998.

(51) Int. Cl.⁷ .................... A61K 31/275; A61K 31/215
(52) U.S. Cl. ........................................ 514/528; 514/529
(58) Field of Search ................................ 514/626, 528, 514/529

(56) References Cited

U.S. PATENT DOCUMENTS

| 3,789,125 A | 1/1974 | Kuger et al. |
| 4,102,948 A | 7/1978 | Feuer et al. |
| 4,218,404 A | 8/1980 | Feuer et al. |
| 5,578,313 A | 11/1996 | Knight et al. |
| 5,643,966 A | 7/1997 | Knight et al. |

FOREIGN PATENT DOCUMENTS

| AU | 655598 | 7/1991 |
| EP | 0 538 330 | 10/1995 |

OTHER PUBLICATIONS

Knight, G.D. et al. Seemingly Diverse Activities of B–Alethine. Cancer Research. Nov. 1, 1994, pp. 5636–5642, vol. 54, see especially Abstract, Figure 1 and pp. 5636–5637.
Delneste Y., Jeannin P. Potier L., Romero P., Bonnefo J–Y: N– acetyl–L–cysteine Exhibits Antitumoral Activity by Increasing Tumor Necrosis Factor Alpha–dependent T–cell Cytotoxicity. Blood. Aug. 1, 1997, pp. 1124–1132, vol. 90., No. 3.
Paul, William E., Fundamental Immunology, Fourth Edition, Pub. Lippincott–Raven pp. 897–900, 1999.

*Primary Examiner*—Theodore J. Criares
(74) *Attorney, Agent, or Firm*—Judith A. Evans; Paul D. Roath (57) ABSTRACT

The present invention relates to methods of using peptide-like compounds, e.g., aminocarboxylic acid amide derivatives, to bias the immune system toward producing, enhancing, or maintaining a polarized Th1 response, and to methods for treating diseases that improve by creating a Th1 response. The invention also relates to a method of treating diseases associated with elevated soluble TNF alpha levels by administering beta-alethine together with NAC to reduce soluble TNF alpha, and to a pharmaceutical composition comprising same. The present compounds can be used to modulate cytokines including IFN-gamma and IL-10.

8 Claims, 1 Drawing Sheet

SMALL MOLECULES THAT ELICIT A POLARIZED TH1 RESPONSE AND FOR MODULATION OF CELLULAR IMMUNITY

This application claims priority to U.S. Provisional Application Nos.: 60/075,966 filed Feb. 24, 1998 and 60/085,474 filed May 14, 1998, which are incorporated herein in their entirety.

FIELD OF THE INVENTION

The present invention relates to therapeutic methods for modulating cellular immunity by administering to an animal or cells from an animal, small molecules that affect the expression of cytokines, activate T cells, and stimulate T cell proliferation.

BACKGROUND OF THE INVENTION

Cytokines are secreted regulatory proteins that control the survival, growth, differentiation and effector function of immune cells. Cytokines encompass those families of regulators variously known as growth factors, colony-stimulating factors, interleukins, lymphokines, monokines, and interferons. They are molecules found in the extracellular medium that interact with specific target cells to communicate information regarding the status of the animal and they result in an appropriate biological response in the target tissue. The producer cells therefore, represent the biological sensors of the animals' condition; the cytokines represent, the method of signal transduction; the receptors represent the means of signal reception; and the responsive cells represent the means of effecting an appropriate biological response. There appear to be very few biological responses that are mediated by only one cytokine and many responses that can be achieved by several different cytokines especially when they are used in combination. Gene deletion experiments reveal that few individual cytokines are absolutely essential for life or even for individual cellular functions.

The key feature of cytokines compared to classical hormones is that they are rarely found in the circulation but rather are produced by cells that are widespread in the body. Cytokines may act in an autocrine, paracrine, or intercrine manner. Cytokine producer cells are often physically located immediately adjacent to the responder cells and they generally secrete very small quantities of cytokine with which the responder cells interact. The responder cells deplete the cytokine they respond to in the process of receptor mediated endocytosis. Many cytokines bind to elements of the extracellular matrix around responder cells further restricting their spread beyond the immediate site and increasing their bioavailability to the responder cells. An extreme example of this bound localization are the cell surface cytokines, such as TNF alpha, which presumably require cell-cell contact for their action. Finally, there are several examples of high levels of circulating soluble cytokine receptors, binding proteins and even receptor antagonists which may serve to inhibit the biological action of a cytokine that does find its way into the serum. Cytokines have very stable structures; most cytokines are relatively small proteins that contain protective carbohydrate and intramolecular disulphide bonds. These elements enhance the solubility, stability, and protease resistance of the cytokines.

Among cytokine producers are T helper (Th) cells which can be divided into two functional subsets, Th1 and Th2, which can be distinguished by the patterns of cytokines they secrete. Th1 cells secrete interleukin (IL)-2, interferon (IFN)-gamma, TNF alpha and beta, and lymphotoxin, among others, and are responsible for the development of the cell-mediated immune response, often called delayed-type hypersensitivity (DTH). This response is critical for the successful removal of intracellular pathogens, such as certain bacteria and viruses. Th2 cells secrete IL-4, IL-5, IL-10, and IL-13 and are responsible for the development of high levels of IgG1, IgA, and IgE production by B cells, and for the activation of effector cells such as eosinophils. Responder cells that respond by producing antibodies are included in class called B-cells.

The commitment to a Th1 or Th2 phenotype appears to occur within the first 48 hours after antigenic stimulation, and is characterized by changes in the expression of particular cell surface markers and cell signaling components. There often exists a relatively large population of activated T cells that represent uncommitted precursors which can become either Th1 or Th2 cells. An area of considerable research has been the study of the role of cytokines in Th1 and Th2 differentiation, which is thought by some to be the most critical factor in determining the nature of the immune response.

Perhaps the most important determinant for the development of stable Th1 and Th2 cells is the cytokine milieu present at the time of initial priming, as well as during the course of a recall response. It has been reported that Th2 cells can be induced by IL-12 to secrete IFN-gamma. Paul, William E., *Fundamental Immunology*, Fourth Edition, Pub. Lippincott-Raven, 897 (1999). Therefore, a method of increasing Th1 cytokines and/or decreasing Th2 cytokines, to generate a polarized Th1 response has clinical significance in stimulating and maintaining cellular immunity.

SUMMARY OF THE INVENTION

Accordingly, it is an object of this invention to provide a method to elicit, enhance or maintain a polarized Th1 response in an animal by administering small molecules such as beta-alethine (BETATHINE™ also Beta LT™ and BT), beta-alanyl taurine, carbobenzoxy beta-alanyl taurine (Taurox™-SB, hereinafter Taurox-SB), and various other aminothiols and amino phosphates. It is another object to provide therapeutic methods that modulate cellular immunity, manipulate cytokine expression, activate T cells, and induce T cell proliferation in order to prevent and treat certain diseases responsive to such therapies. It is a further object to provide pharmaceutical compositions to treat pathogen-induced infections.

It is an object of the invention to provide a method for biasing the immune system toward producing, enhancing or maintaining a polarized Th1 response in an animal. It is another object of the invention to provide a method of preventing or treating diseases that respond to an increase in one or more Th1 cytokines. It is also a specific object to provide a method of producing, enhancing or maintaining cellular immunity by administering one or more compounds of Formula I as defined in this application. It is a further object to provide a method of activating T cells, stimulating or increasing T cell proliferation, increasing or stimulating T cell-dependent cytotoxicity and increasing the production of cytotoxic T lymphocytes in an animal.

It is a further object of the present invention to provide a method of preventing or treating pathogen-induced infections by administering to an animal a combination of one or more compounds of Formula I as defined in the following section, and one or more antimicrobial agents such as antibiotics, antiviral agents, or antifungal agents. It is a further object to provide a pharmaceutical composition for treating or preventing pathogen-induced infections by administering to an animal a combination of one or more compounds of Formula I as defined in the following section, and one or more antimicrobial agents.

It is another object of the present invention to provide a method ti prevent or treat ischemia or reperfusion injuries in an animal by administering one or more compounds of Formula I. Finally, it is yet another object to provide a method and a pharmaceutical composition to decrease soluble TNF in an animal.

Another aspect of the present invention is to provide a set of compounds that modulate the immune response causing a coordinated increase or decrease in various cytokines and other signaling molecules to obtain a desired effect. It is an aspect to cause an increase in pro-inflammatory cytokines in unstimulated cells needing to produce more cytokines but a decrease in several signalling agents in cells that are previously overstimulated. It is another object to provide a method of modulating the immune system toward or away from producing, enhancing or maintaining a polarized Th1 response in an animal, and methods for increasing or decreasing cellular immunity in an animal

DETAILED DESCRIPTION OF THE INVENTION

According to the present invention, it has been discovered that beta-alethine (Beta LT™, BETATHINE™, BT) beta-alanyl taurine, Taurox-SB, carbobenzoxy beta-alanyl taurine, and various other aminothiols, Taurox™ compounds and amino phosphates of Formula I, modulate immune cell expression of various cytokines and can be administered to an animal to bias the immune system toward producing a polarized Th1 response. They also increase T cell activation and proliferation.

In other embodiments, the compounds of Formula I can be administered to an animal to enhance or maintain a Th1 response, to stimulate or enhance IFN-gamma production to treat diseases responsive, or to enhanced IFN-gamma.

Another embodiment of the present invention involves administration of compounds of Formula I to depress IL-10 expression to treat diseases caused or exacerbated by over-expression of IL-10. The compounds of Formula I also stimulate cytotoxic T lymphocyte activity which together with IFN gamma fight cellular viral infections. The compounds of Formula I also increase surface TNF alpha which is associated with fighting bacterial, parasitic and viral infections. It has also been discovered, according to the present invention, that the combination of beta-alethine BT plus N-acetyl cysteamine (NAC) completely eliminates soluble TNF alpha release from T cells, which has adverse proinflammatory effects. The compounds of Formula I significantly increase surface TNF alpha expression on immune cells without increasing soluble TNF alpha.

In related work, beta-alethine was found to have a variety of diverse effects, including use as a nontoxic anti-cancer agent, Knight et al., U.S. Pat. No. 5,643,966, and U.S. application Ser. Nos. 08/346,177, 08/468,043, and 08/468,041 which are incorporated herein by reference in their entirety for all purposes. BT has also been shown to be useful as an adjuvant in vaccines to stimulate antigen-specific immunoglobulin synthesis in vivo. U.S. application Ser. Nos. 08/733,174; 08,466,143; 08/463,731, and 08/463,784.

In other related work, beta-alanyl taurine and carbobenzoxy beta-alanyl taurine (Taurox-SB) have anticancer and immunostimulatory activity. U.S. Pat. Nos. 5,370,868; 5,578,313; and U.S. Ser. No. 08/469,697, also incorporated herein by reference in their entirety.

Beta-alethine and Taurox-SB. come within Formula I, shown below:

(I)

In Formula I, A is a group of the formula —$PO_3H$, —$SO_3H$, —OPO—$(OH)_2$, —$OSO_2OH$, or —SH, or pharmaceutically acceptable salt thereof or physiologically hydrolyzable derivative thereof, or disulfide thereof when A is —SH. Suitable salts include sodium, potassium, calcium and zinc. Suitable hydrolyzable derivatizing groups include esters, such as substituted or unsubstituted lower alkyl (eg $C_1$ to $C_4$) or arylalkyl (eg benzyl) esters.

$R_1$ is H, a linear or branched lower alkyl, for example, a $C_1$ to $C_6$ alkyl, arylalkyl, for example, wherein the alkyl moiety is $C_1$ to $C_4$ alkyl and the aryl moiety is a substituted (eg lower alkyl or halogen) or unsubstituted phenyl group, or alkenyl (for example, $C_2$–$C_6$ alkenyl).

$R_2$ is H, a linear or branched lower alkyl, for example, a $C_1$ to $C_6$ alkyl, an alkenyl, for example, a $C_2$–$C_6$ alkenyl, an arylalkyl, for example, wherein the alkyl moiety is a $C_1$ to $C_4$ alkyl and the aryl moiety is a substituted (e.g., lower alkyl or halogen) or unsubstituted phenyl group; or an acyl, for example, acetyl, benzoyl, arylsulfonyl (for example, when the aryl moiety is phenyl); a carbonate ester such as alkoxy-carbonyl (including, $C_1$–$C_7$ alkoxy carbonyl,for example, —$OCOC(CH_3)_3$); allyloxy carbonyl (e.g., —$OCOCH_2CH=CH_2$); cycloalkoxycarbonyl (eg when the ring is $C_3$–$C_8$ ($C_5$–$C_6$ being preferred) and when the alkoxy moiety is $C_1$–$C_8$ (for example —$OCOCH_2C_5H_9$); or an unsubstituted arylalkoxycarbonyl (for example —$OCOCH_2C_6H_5$) or a substituted arylalkoxycarbonyl wherein the substituent is, for example, a halogen, a nitro group, an amino group or a methoxyl group.

Alternatively, $R^1$ and $R^2$ taken together form, with the nitrogen to which they are attached, a 5 to 7 membered ring (for example, $R^1$ and $R^2$ taken together can be —$(CH_2)_4$—, —$(CH_2)_5$ or —$(CH_2)_6$—).

$L^1$ and $L^2$ are hydrocarbon linking groups, for example, a linear or branched chain alkyl of the formula —$(C_nH_{2n})$— wherein n is, for example, 1 to 8 in the case of $L^1$ and 2 to 8 in the case of $L^2$ except when A is —$PO_3H$ or —$SO_3H$ in which case n can be 1–8; a cycloalkyl of 3 to 8 carbon atoms, preferably 5 or 6 carbon atoms; or an interphenylene (eg Advantageously, $L^1$ and $L^2$ are —$(C_nH_{2n})$— wherein n is 1 to 8 in the case of $L^1$ or 2 to 8 in the case of $L^2$ except when A is —$PO_3H$ or —$SO_3H$ in which case n can be 1–8

(examples of branched chain alkyls include —CH$_2$CHR—, —CH$_2$CHRCH$_2$—, —CHRCH$_2$CH$_2$—, and —CH$_2$CH$_2$CHR— wherein R is an alkyl group and wherein the total number of carbon atoms, including R, does not exceed 8.)

A particular group of compounds of the invention is of the Formula (I) wherein A, R$^1$, R$^2$, L$^1$ and L$^2$ are as defined above in a first embodiment with the proviso that when A is —SO$_3$H or pharmaceutically acceptable salt thereof or physiologically hydrolyzable derivative thereof, when one of R$^1$ and R$^2$ is H, and when L$^1$ and L$^2$ are (CH$_2$)$_2$, then the other of R$^1$ and R$^2$ is not H.

Another particular group of compounds of the invention is of the Formula (I) wherein A, R$^1$, R$^2$, L$^1$ and L$^2$, are as defined above in the first embodiment with the proviso that when A is —SO$_3$H or pharmaceutically acceptable salt thereof or physiologically hydrolyzable derivative thereof, one of R$^1$ and R$^2$ is H, and L$^1$ and L$^2$ are (CH$_2$)$_2$, then the other of R$^1$ and R$^2$ is not C$_6$H$_5$CH$_2$OCO—.

A further particular group of compounds of the invention is of the Formula (I) wherein A is a group of the formula —PO$_3$H or —OPO(OH)$_2$, more particularly —PO$_3$H, or a pharmaceutically acceptable salt thereof or a physiologically hydrolyzable derivative thereof, and wherein R$^1$, R$^2$, L$^1$, and L$^2$ are as defined above in the first embodiment.

Another particular group of compounds of the invention is of the Formula (I) wherein A is a group of the formula —SO$_3$H or —OSO$_2$OH, more particularly —OSO$_2$OH, or pharmaceutically acceptable salt thereof, or physiologically hydrolyzable derivative thereof, and wherein R$^1$, R$^2$, L$^1$ and L$^2$ are as defined above in the first embodiment. The provisos above can apply to this group of compounds as well.

A further particular group of compounds of the invention is of the Formula (I) wherein at least one of R$^1$ and R$^2$ is an alkyl, advantageously a lower alkyl (eg C$_1$ to C$_6$), and wherein A, L$^1$, L$^2$ and the other of R$^1$ and R$^2$ are as defined above in the first embodiment.

Another particular group of compounds of the invention is of the Formula (I) wherein R$^1$ is an alkyl and R$^2$ is acyl and wherein A, L$^1$ and L$^2$ are as defined above in the first embodiment.

A further particular group of compounds of the invention is of the Formula (I) wherein L$^1$ is —(CH$_2$)— and wherein A, R$^1$, R$^2$, and L$^2$ are as defined above in the first embodiment.

Yet another particular group of compounds of the invention is of the Formula (I) wherein R$^1$ and R$^2$ are taken together and form, with the nitrogen to which they are attached, a 5 to 7 membered ring, and wherein A, L$^1$ and L$^2$ are as defined above in the first embodiment.

The present compounds can also be covalently bound to proteins, for example, antigens or other immunologically active proteins, or cell targeting proteins. Such conjugates can be synthesized using techniques known in the art.

The compounds of the present invention can be prepared using, for instance, methods provided in the Examples and in U.S. Pat. Nos. 4,102,948 and 4,218,404, as appropriate. Beta-alethine (also called BETATHINE™ and BetaLT™ and beta-alanyl cysteamine disulfide) is a disulfide that is a dimer composed of two small thiols(H$_2$NCH$_2$CH$_2$(C=O)NHCH$_2$CH$_2$S)$_2$. Both beta-alethine and its precursor beta-aletheine are stabilized as their acid salts, particularly their hydrogen halide salts. Various techniques for the synthesis of beta-alethine have been described in the literature based on deblocking of (N,N=-BIS-CARBOBENZOXY)-blocked beta-alethine. It is preferred that beta-alethine for use in the compositions and methods of this invention be prepared by processes which ensure purity of the product and preferably also maximize yield. The method for making a high-yield, high-purity beta-alethine suitable for pharmaceutical use is in the Examples that follow.

Both the disulfide and thiol forms or all of the molecules of Formula I are included in the invention; the use of a name referring to either the thiol of disulfide is meant to include both forms.

In toxicity studies performed to date, BT has exhibited extremely low toxicity. An independent, contract facility (good laboratory practice) GLP administered single bolus intravenous doses of BT to CD-1 mice (at least one male and one female each weighing 22–30 grams). The mortalities were 0/2, 1/3, and 2/2 at 67, 333, and 667 mg/kg, respectively. Convulsions and tremors were observed at the 333 mg/kg dose. When the dose was lethal, death was immediate. The surviving animals were normal throughout the 2-week observation period. No gross pathology was observed at necropsy. Thus, the acute, intravenous LD$_{50}$ for beta-alethine in mice is estimated to be greater than 100 mg/kg. These results suggest that BT may have a high therapeutic index.

Taurox™ is a trade name that refers to compounds having some structural characteristics analogous to beta-alanyl taurine. The structures of BT, beta-alanyl taurine, carbobenzoxy-beta-alanyl taurine, Taurox™-SBand other Taurox™ compounds fall within Formula I.

Effects on Cellular Immunity

It has now been discovered that the compounds of Formula I produce a polarized Th1 response in human peripheral blood mononuclear cells which (includes composed of) very approximately 60% T cells, 13% monocytes, and 17% B cells, and 10% natural killer cells.

Compounds of Formula I cause a coordinated alteration in Th1 cytokines, potentially including Interferon gamma (IFN-gamma), Interleukin 2 (IL-2), TNF alpha and beta, and Lymphotoxin, from unstimulated human T cells and monocytes and bias the immune system toward a polarized Th1 response. (see FIG. 1.) It has been further shown that beta-alethine also depresses the levels of the major Th2 cytokine IL-10, which cytokine is required for maintaining a Th2 response over time.

It is during the initial response to antigen in the peripheral lymphoid tissues that the differentiation of T cells into an inflammatory T cell (Th1) or a T cell (Th2) that stimulates antibody production by B cells is determined. A Th1 response is dominated by macrophage activation, while a Th2 response is dominated by antibody production. The mechanism controlling this step in T cell differentiation is not fully defined; however, it is influenced profoundly by the type of cytokines present during the initial proliferative phase of T cell activation. Thus, manipulating the amount of cytokine produced will affect the commitment of T cells to either a Th1 or Th2 cell type. T cells initially in the presence of INF-gamma tend to develop into inflammatory T cells, in part because INF-gamma inhibits the proiferation of helper Th2 cells.

Soluble TNF alpha release by T cells causes local protective effect, however, it can have damaging effects when released systemically. Surface TNF alpha is associated with anti-cancer activity of T cells.

Cytokines produced by each of Th1 and Th2 cell types have regulatory effects on the other cell type. For example, IFN-gamma was shown to have a negative effect on the proliferation of Th2 cells and IL-10 inhibits IFN-gamma secretion by Th1 cells which inhibits Th1 differentiation. IL-10 also inhibits production of the important Th1 cytokine IL-12 by macrophages and dendritic cells. Therefore there is a need for a means to downregulate IL-10 production in order to generate or enhance or maintain a functional Th1 response. This is especially important to develop primary immunity to a variety of infectious pathogens including bacteria, viruses, parasites and fungi. Paul at 899.

IFN-gamma, in turn, has a direct inhibitory effect on Th2 proliferation. This phenomenon was termed crossregulation. Morel, P. A., et at., Critical Reviews in Immunology, 18:275–303 (1998).

Th1 and Th2 cells exert indirect effects on each other by influencing the Antigen Prescribing Cells (APC) that with each prefers to interact. Thus, Th2 cytokines (IL-4, IL-10, and IL-13) inhibit the function and activation of macrophages, which are the main source of IL-12, necessary for the development and maintenance of Th1 responses. In contrast, IFN-gamma produced by Th1 cells inhibits the proliferation and function of B cells, which facilitate the successful development of Th2 responses.

It has now been discovered that in conditions of understimulation or where there is a need for activated T cells, the compounds of Formula I create a coordinated increase in Th1 cytokines and immune signals that increase cellular immunity, and bias the immune system toward producing, enhancing, or maintaining a polarized Th1 response by causing a coordinated increase in Th1 cytokines. For example, Taurox-SB and beta-alethine both increased messenger RNA for the Th1 cytokines IFN-gamma, TNF alpha and Lymphotoxin-beta from unstimulated human T cells. Beta-alethine also increased IL-2 and significantly depressed the production of the dominant Th2 cytokine IL-10, which cytokine is required to maintain a sustained Th2 response. 20 mM BT and 1.4 mM Taurox-SB increased message for TNF alpha relative to that of TGF beta in both unstimulated and stimulated T cells. While TGF beta is a pleotropic cytokine, it is often considered to be immunosuppressive (Sporn and Roberts, 1989).

Although transcription of messenger RNA for IL-10 was significantly decreased by BT, transcription of messenger RNA for the Th2 cytokines Interleukins 4 and 5 was paradoxically enhanced in the presence of BT. It is important to emphasize that IL-4, although a Th2 cytokine, has a positive effect on Th1 cell proliferation. Therefore, the increase in IL-4 does not diminish, but may even enhance the overall effect of the compounds of Formula I to induce a Th1 response. IL-2 has a positive effect on Th-2 cells even though it is a Th1 cytokine. For the reasons set forth above, the overall result of unstimulated T cell exposure to compounds of Formula I is a coordinated increase in Th1 cytokines and/or a polarized Th1 response.

Thus, a component of the present invention is directed to methods of modulating the immune system to produce, enhance, or maintain a coordinated polarized Th1 response in an animal by administering one or more compounds of Formula I. In a most preferred embodiment, the compound is BT or Taurox-SB administered in the femtogram/kg body weight to miligram/kg body weight range. According to the present invention, a polarized Th1 response is produced, enhanced or maintained to treat pathogen-induced infections including those from bacteria, viruses, fungi or parasites.

One such disease is mycobacteria infections including tuberculosis and leprosy. The inhibition of Th2 cells by IFN-gamma has been shown to be of relevance in vivo in the case of infection with *Mycobacterium leprae*. This infection results in diseases that have two distinct phenotypes. Tuberculous leprosy represents a Th1-dominated response, and is characterized by granuloma formation and low bacterial load. Lepromatous leprosy is dominated by Th2 cells and characterized by antibody production and high bacterial load. Cytokines have been used in the treatment of lepromatous leprosy and in particular, IFN-gamma has been shown to effectively inhibit Th2 responses in lepromatous lesions, thereby allowing the emergence of newly differentiated Th1 cells. Compounds of Formula I can therefore be used to treat or prevent reoccurence of lepromatous leprosy by producing a Th1 response. Listeria and malaria treatments are also provided.

In a preferred embodiment of the present invention, one or more of the compounds of Formula I is administered together with one or more antibiotics to treat pathogen-induced infections. Another preferred embodiment is a pharmaceutical composition for treating microbial- or bacterial-induced infections, comprising one or more antimicrobials and one or more of the compounds of Formula I in amounts sufficient to treat the infection. The coadministration of beta-alethine and antibiotics will enhance the ability of the host to fight infection and thereby minimize the chance of creating resistant strains.

An increase in IFN-gamma brought about by the present invention causes macrophage activation which provides increased cell mediated immunity against extracellular bacteria, especially gram negative bacteria, as well as against intracellular bacteria.

According to the present invention, viral infections are also treated. Cytotoxic T Lymphocytes (CTLs) are the primary immune effector cells responsible for surveillance against viral infections. CTLs are capable of recognizing virally infected host cells and destroying them by mechanisms such as release of granule contents. Both IFN-gamma and IL-2 play an important role in CTL differentiation. It has been discovered that compounds of Formula I, including beta-alethine [BetaLT™, BETATHINE™] and Taurox-SB, contribute to effective development of CTLs thereby enhancing the anti-viral immune response. Therefore, in yet another embodiment of the present invention, compounds of Formula I can be administered to prevent or treat viral-induced infections. Further, one or more compounds of Formula I can be combined with one or more anti-viral agents to form an anti-viral pharmaceutical composition.

The invention is also directed to methods of treating diseases associated with deficient cellular immunity by administering an amount of one or more compounds of Formula I sufficient to enhance cellular immunity. In another aspect of the present invention, compounds of Formula I are administered to a patient prior to and immediately after surgery to prevent the development of a pathogen-induced infection by modulating cellular immunity to elicit a polarized Th1 response.

In another embodiment, certain ischemic diseases are treated. Hypoxia is a cellular stress condition associated with an increase in the level of the cytokine IL-10. It is known that ischemic acute tubular necrosis in mouse, ischemia associated with cardiopulmonary bypass in man and liver ischemia reperfusion in mouse and man have all been found to be associated with IL-10 overexpression. Morel, P. A., et al. Critical Review Immunology 18:275–303 (1998). Therefore, it is another aspect of the present invention to provide a method of treating ischemic diseases by administering to a patient in need of such treatment one or more compounds of Formula I. By way of example, compounds of Formula I can be administered before or after surgery to prevent ischemia in patients undergoing cardiopulmonary bypass, liver ischemia reperfusion or other procedure for which there is an associated risk of an ischemic event.

Another aspect of the invention is the discovery that the compounds' action is dependent on the underlying state of the immune system. In cells that are already overly or highly stimulated by PMA and ionomycin the compounds do not cause a coordinated increase in Th1 cytokines rather their action modulates the immune response and decreases many of the Th1 and other cytokines being produced at elevated levels by the overly stimulated cells. The present invention is thus a set of compounds that modulate the immune response causing a coordinated increase or decrease in various cytokines and other signaling molecules to obtain a desired effect. One remarkable aspect of the invention is that the compounds, in combination with the immune system, demonstrate an "intelligence" causing an increase in pro-inflammatory cytokines in unstimulated cells needing to produce more cytokines but a decrease in several signalling agents in cells that are previously overstimulated. The immune system normally shows this innate intelligence leading to a balance between auto- or hyperimmunity and insufficient immune response. In many diseases (involving either increased or decreased immunity) the ability to maintain this modulated balance is decreased or lost; the current invention assists in restoring the balance and obtaining normal immune function.

The appropriate doses of the compounds of Formula I for the uses described above, for example to elicit, enhance or maintain a Th1 response, can be determined by routine experimentation. Contemplated dosages of the above-identified drugs can range, from femtograms/kg body weight (b.w.) to nanograms/kg b.w. in the case of slow disease prevention or maintenance therapy, to about 100 mg/kg b.w. in more aggressive disease treatment regimens where higher amounts of the drugs may be necessary. The maximum tolerated dose may be required in certain circumstances.

A series of experiments were conducted to determine the ability of the compounds of Formula I, including BT, Taurox-SB and the thiol antioxidant NAC to regulate expression of the Th1 cytokine TNF alpha in T cells and monocytes.

TNF-alpha (Tumor Necrosis Factor-alpha), or cachetin is a pleiotropic cytokine that is a primary mediator of numerous immune functions, including hemorrhagic tumor necrosis/cytotoxicity, inflammation and regulation of anti-viral and immune proliferative and activation responses. As a central player in the cytokine network, TNF alpha has been implicated in a variety of disease states, including cachexia, endotoxic (septic) shock, acute respiratory distress syndrome and a number of necrotic, proliferative and autoimmune diseases. TNF alpha is expressed as a membrane or as a soluble protein. Soluble TNF alpha(17 kD) results from the shedding of the membrane form (25 kDa) mediated by a Zn++-dependent endopeptidase TNF alpha converting enzyme (TACE) which is a metalloproteinase. Soluble TNF alpha has potent proinflammatory properties. Both membrane and soluble TNF alpha mediate cell death and are crucial to initiate an antitumoral response. Specific, high affinity TNF alpha receptors mediate signal transduction responsible for the biologic effects of TNF alpha. TNF alpha signaling is mediated by TNF-RI (75–80 kDa) and TNF-RII (55–60 kDa). The two TNF receptors appear to be distributed broadly, but differentially, in various tissues. The most abundant form of TNF receptor on the surface of activated T cells has been reported to be the 80 kDa R-I form.

Soluble TNF alpha neutralizes the activity of TNF alpha by inhibiting its binding to membrane receptors. Both membrane and soluble TNF alpha act on TNF alpha receptor-bearing T cells by increasing interleukin 2 (IL-2) production, CD25 expression and proliferation. IL-2, in turn increases TNF alpha receptor expression.

Surface TNF alpha is involved in killing by cell-cell contact after interaction with membrane TNF alpha receptors expressed on the target cells. TNF alpha exhibits a potent cytolytic and cytostatic activity towards a variety of tumor cell lines and virally infected cells. NAC has been used clinically as an immunomodulator; it has antimutagenic and anticarcinogenic properties that include the ability to reduce tumor invasion and metastasis. Various T cell functions such as proliferation, IL-2 production, and enhanced natural killer cell and lymphokine activated killer cell (LAK) levels, have all been reported to be enhanced by NAC and glutathione in combination with different stimuli.

It has been discovered that both human monocytes and T cells stimulated with PMA/ionomycin in vitro and treated with beta-alethine significantly and consistently display upregulated expression of surface TNF alpha over levels observed in cells treated with PMA/ionomycin alone. Taurox-SB increased surface TNF alpha on T cells when used alone, even in the absence of PMA/ionomycin stimulation. Both the BT- and the Taurox™-SB-induced increase in TNF-alpha was associated with elevated messenger RNA expression. The increase in surface TNF was associated with dramatically elevated expression of TNF-RI on activated T-cells. The effect of BT on soluble TNF alpha was also studied. According to the present invention, it was unexpectedly discovered that the combination of BT and NAC used together effectively eliminated detectable release of soluble TNF alpha from stimulated peripheral blood lymphocytes. It is therefore another embodiment of the present invention to treat an animal with elevated soluble TNF alpha with a combination of NAC and beta-alethine. The present invention is also directed to a composition for lowering soluble TNF or treating a condition associated with elevated levels of soluble TNF alpha comprising beta-alethine and NAC. Such conditions include rheumatoid arthritis and anaphylatic shock.

According to the present invention, BT was found to increase T cell-dependent cytotoxicity toward malignant HL60 target cells. This activity was inhibited in the presence of anti-TNF alpha antibodies. The anticancer effects of the antioxidant thiol NAC are reported to be associated with an NAC-induced increase in T cell cytotoxicity toward tumors which correlates with an increase in surface TNF alpha expression.

TNF alpha levels have also been observed to positively correlate with a favorable clinical prognosis in some melanomas.

According to the present inventions, both BT and Taurox-SB in the milimolar range increased cytotoxic T lymphocyte (CTL) activity as was measured by N-a-benzyloxycarbonyl-L-lysine thiobenzyl ester (BLT) esterase activity. In addition to generation of CTLs, BT also increased T cell-dependent cytotoxicity toward the HL60 targets. This activity was inhibited by the presence of neutralizing anti-TNF alpha antibodies (data not shown). Therefore, it is another embodiment of the present invention to administer a compound of Formula I to increase the CTLs. In a preferred embodiment, the compound is BT or Taurox-SB.

Surface TNF alpha is involved in many immune responses, including for example active phagocytosis of extracellular organisms especially gram negative bacteria and viruses. Interferon gamma is also very important to induce macrophage activation and to promote phagocytosis of extracellular organisms especially gram negative bacteria and viruses. Therefore, increasing surface TNF alpha expression according to the present invention has important clinical use. This use is particularly great if surface TNF alpha and/or TNFR-I can be selectively increased without increasing soluble TNF alpha which is associated with adverse proinflammatory effects, as is the case with the compounds of the present invention.

The present invention for increasing surface TNF alpha expression has advantages and other effects. Human Recombinant TNF alpha is produced in E. coli as a 17 kDa protein containing 157 amino acid residues and is species cross-reactive. However, the adverse proinflammatory properties of soluble TNF alpha make it undesirable to inject human recombinant soluble TNF alpha. So far, TNF alpha has been used only in a limited fashion for treatment of neoplasia by 57. Its use is limited to regional limb perfusion, intercavitary or direct tumor injection. The unexpected discovery according to the present inventions, that compounds of Formula I, especially BT, selectively increase surface TNF alpha expression on activated T cells without increasing the expression of soluble TNF alpha, has important therapeutic implications.

Our results show that small sulfur-containing molecules administered without a free thiol, such as the disulfide BT, can also increase surface TNF alpha at concentrations equivalent to those of free thiols like NAC.

In another embodiment of the present invention, compounds of Formula I are administered together with one or more metalloproteinase inhibitors to elicit, maintain, enhance a Th1 response without increasing levels of soluble TNF.

It has been discovered that Taurox-SB administered to an animal caused an increase in T cell activation as determined by enhanced expression of the activation marker CD69. Taurox-SB also increased human T cell proliferation, as was detected by incorporation of 3H-thymidine. Therefore, the compounds of the present invention can be used to activate T cells and enhance proliferation.

The compounds of Formula I for use in the various embodiments of the present invention, can be administered as needed by observing standard indicia of the progress of the disease using methods known to persons of ordinary skill in the art. The drugs are preferably administered on a daily or alternate-day regimen as described more fully below, until the desired results are achieved. Other regimens, such as weekly or biweekly regimens may suffice, particularly when a positive response is readily apparent. Decreases in dosages of the drugs, the frequency of administration, or both, can be made as normalization progresses. The methods of the present invention are not limited to any particular amount of the above-identified drugs, as therapeutically effective amounts can be determined by routine testing.

The compounds of the present invention are typically used in the form of a pharmaceutical composition comprising one or more compounds of Formula I, or salt or hydrolyzable derivative thereof, together with a pharmaceutically acceptable diluent or carrier. The compositions of the present invention are also so formulated. The drugs may be administered topically, orally, rectally, intravaginally intravenously, intraperitoneally, subcutaneously, intramuscularly or intranasally, or by other means known in the art, as appropriate for the effect sought. The drugs can also be administered transdermally using, for example, transdermal patches or transmucosally via sprays or other application. The drugs can be present in dosage unit form, for example, as a tablet, capsule or suppository, or formulated so as to be suitable for topical application (e.g., as a gel, cream, lotion or ointment). The compounds and compositions of the present invention can also be administered in liposomes, microemulsions, sprays, or via any alternative delivery system.

Alternatively, the drugs can be present as a solution or suspension (e.g., sterile) suitable for administration by injection, inhalation, intranasally or dropwise to the eye or other sites as appropriate. The drugs of the invention can be prepared as a slow release formulation appropriate for internal or external use. Using techniques known in the art, they can also be trapped in or bound to a polymer, a solid support, a liposome or a gel.

Beta-alethine, Taurox™ compounds and other compounds of Formula I, can be administered together with additional active agents such hormones, vitamins, cytokines, enzyme regulators, regulatory macromolecules, regulatory thiols or other small molecules.

The compounds and compositions of the present invention are suitable for therapeutic use in humans and for veterinary treatment of similar conditions affecting warm-blooded animals, such as dogs, cats, horses, birds and cattle and for reptiles, and fish. For such purposes, the compounds can be administered in an analogous amount and manner to those described above for administration to humans.

Therapeutic administration of the beta-alethine and the Taurox-SB compounds may be performed by methods known to those skilled in the art including orally, transmucosally, sublingually, parenterally, intravenous, intramuscular or subcutaneous routes, direct delivery into the tumor, direct delivery into an affected body cavity by infusion, and oral or rectal administration.

A therapeutic dose, of the compounds of Formula I for use with the methods and compositions of the present invention, is an amount that is effective to modulate cytokine production by immunocytes, or increase cytotoxic T lymphocytes, or activate T cells, or increase cellular immunity, or increase PMBC proliferation. The amount of the compounds to be used and the frequency of exposure for statistically significant effects can be readily determined by one skilled in the art and will vary with the type of disease being treated or the cell type in the case of ex vivo therapy, and the effect sought. The term "statistically significant" is well known to those skilled in the art.

Cells can be grown or stored in the presence of the compounds using any of a variety of available techniques, including growth on plastic or glass or other support (e.g., beads or hollow fibers), growth in suspension (e.g., in liquid or semisolid medium), growth in a bioreactor, or storage in a frozen or dried state. Primary cultures or serial cultures, or otherwise, can be used.

The amount of the compound of the invention to be used and the frequency of exposures or statistically significant effects can be readily determined by one skilled in the art and will vary with the cell type, the compound used and the effect sought. In determining optimum concentrations, appropriate in vitro assays are run in the femtogram/ml to mg/ml range.

Various aspects of the present invention are described in greater detail in the non-limiting Examples that follow.

Certain of the synthetic procedures described below correspond to those described by Knight et al, Cancer Research 54:5623 (1994) or in U.S. Pat. No. 4,218,404, or represent modifications thereof. These references are incorporated by reference herein in their entirety. In addition, the disclosures of WO 92/00955 and PCT/US91/04725 are relevant here, including the portions therein that relate to syntheses, therapeutic regimens and cell culture treatment protocols, those regimens and protocols being applicable to the drugs of the present invention. These references are also incorporated by reference herein in their entirety.

This application claims priority to U.S. Provisional Application Nos.: 60/075,966 and 60/085,474, which are incorporated herein in their entirety.

EXAMPLES

Example I

Synthesis of N-Carbobenzoxy-b-Alanyl-Taurine Zinc Salt

Method I
Preparation of N,N'-bis(CBZ)-b-Alethine from N-CBZ-b-Alanine

To a 250 ml round bottom flask were added a stir bar, N-CBZ-alanine 5.805 g, 26.008 mmol), N-hydroxysuccinimide (2.993 g, 26.008 mmol, 1 eq.), and 1,3-dicyclohexylcarbodiimide (5.366 g, 26.008 mmol, 1 eq.). The flask was sealed with a septum and purged with argon. $CH_2Cl_2$ (86 ml) was then added and the mixture stirred overnight at room temperature (rt). All of the solids did not dissolve upon addition of $CH_2Cl_2$. The solids were then removed via vacuum filtration through a pre-argon-purged medium glass fritted buchner funnel. The funnel was equipped with an argon purge funnel and a 500 ml round bottom flask containing a stir bar and cystamine 2HCl (1.464 g, 6.502 mmol, 0.25 eq.). The flask and solids (white) were then rinsed with 3×15 ml $CH_2Cl_2$. The filtrate was colorless to light yellow. The flask was removed from the buchner, sealed with a septum and purged with argon. To the stirring solution was added $Et_3N$ (2.9 ml, 20.806 mmol, 0.8 eq.). All of the solids did not dissolve. The reaction was stirred overnight at room temperature. The product was then collected using an 11 cm buchner funnel with #541 Whatman filter paper. The flask and solids (white) were rinsed with 3×15 ml $CH_2Cl_2$. The filtrate was colorless to yellow. The solids were placed in a 250 ml round bottom flask and dried under high vacuum overnight. The crude product weight was determined and DMSO (0.3 g/ml) was added and heated to 70/C–90/C to dissolve the solids with the aid of stirring. $H_2O$ (0.12 g/ml) was then added slowly with vigorous stirring. The mixture was cooled to room temperature and collected after 3 hours using an 11 cm buchner funnel with #541 Whatman filter paper. The solids (white) and flask were rinsed 3×15 ml $CH_2Cl_2$ $H_2O$ followed by 2×15 ml EtOAc. The solids were chopped-up with a spatula and dried under high vacuum in a 250 ml round bottom flask. The recovery was 3.568 g corresponding to a 97.5% yield.

Preparation of N-Carbobenzoxy-b-alanyl-taurine Zinc Salt from N,N'-bis(CBZ)-b-Alethine (Small Additions of ZnO or $Ca(OH)_2$)

To a 250 ml erlenmeyer flask were added a stir bar, N,N'-bis(CBZ)b-alethine (2.524 g, 4.486 mmol), dimethylsulfoxide (2.5 ml), N,N-dimethylformamide (2.5 ml), pyridine (3.2 ml), $CHCl_3$ (75 ml), and $H_2O$ (150 ml). The mixture was stirred vigorously giving an emulsion (not all solids dissolved). A pH meter was immersed in the aqueous phase. The pH was near 7.3 to 7.7. $I_2$ (7.97 g, 31.401 mmol, 7 eq.) was then added. Initially the organic phase was red and the aqueous phase was colorless. During the reaction, the color of the aqueous phase darkened to red and the emulsion subsided. The pH dropped to 5.7 within 10 minutes of adding $I_2$. ZnO (100–200 mg, 0.3–0.6 eq.) was added in portions to keep the pH between 5.7 and 6.0. After ~3.5 hours, the pH stabilized and the reaction was allowed to stir for an additional 2 hours (5.5 h total reaction time). The phases were separated (organic was dark red) and the aqueous phase was washed wiTh10 ml $CHCl_3$. The aqueous phase (light red) was extracted additionally with $CHCl_3$ using a continuous liquid/liquid extractor overnight. The aqueous phase (colorless to very light pink) was separated, partially evaporated on a rotary evaporator to remove dissolved organics, shelf frozen, and lyophilized. The residue (golden brown) was dissolved in 1 ml $H_2O$ and 3 ml acetonitrile and added to 100 ml acetonitrile. The white precipitate was collected on a #541 Whatman filter paper and rinsed with 40 ml acetonitrile. The recovery was 1.676 g of white solids corresponding to a 52% yield (N-carbobenzoxy-b-alanyl-taurine zinc salt).

Preparation of N-Carbobenzoxy-b-alanyl-taurine Zinc Salt from N,N'-bis(CBZ)b-Alethine (ZnO Added Initially)

To a 125 ml erlenmeyer flask were added a stir bar, N,N'-bis(CBZ)b-alethine (809 mg, 1.438 mmol), dimethylsulfoxide (0.8 ml), N,N-dimethylformamide (0.8 ml), pyridine (1.0 ml), $CHCl_3$ (24 ml), $H_2O$ (80 ml), and ZnO (526 mg, 6.470 mmol, 4.5 eq.). The mixture was stirred vigorously giving an emulsion (not all solids dissolved). $I_2$ (3.28 g, 12.904 mmol, 9 eq.) was then added. Initially, the organic phase was red and the aqueous phase was colorless. During this reaction, the color of the aqueous phase darkened to red and the emulsion subsided. The mixture was stirred overnight. The phases were then separated (organic was dark red) and the aqueous washed wiTh20 ml $CHCl_3$. The aqueous phase (light red) was extracted additionally with $CHCl_3$ using a continuous liquid/liquid extractor overnight. The aqueous phase (colorless to very light pink) was separated, partially evaporated on a rotary evaporator to remove dissolved organics, shelf frozen, and lyophilized. The residue (golden brown) was dissolved in 0.5 ml $H_2O$ and 2 ml acetonitrile and added to 75 ml acetonitrile. The white precipitate was collected on a #541 Whatman filter paper and rinsed wiTh20 ml acetonitrile. The recovery was 630 mg of white solids corresponding to a 61% yield (N-carbobenzoxy-b-alanyl-taurine zinc salt).

The $^{13}C$ NMR spectral data were as follows:

| Signal | DMSO solvent: C—H coupled |
| --- | --- |
| 1 | 48.4 |
| 2 | 33.8 |
| 3 | 172.2 |
| 4 | 34.6 |
| 5 | 36.4 |
| 6 | 156.4 |
| 7 | 65.4 |
| 8 | 135.0 |
| 9 | 125.8 |
| 10 | 126.5 |
| 11 | 128.0 |

Method IIa
Preparation of N-Carbobenzoxy-β-alanyl-taurine (Free Acid and Zinc Salt) from N-(CBZ)-β-Alanine The N-(CBZ)-β-alanine (563 mg, 2.522 mmol), N-hydroxysuccinimide (290 mg, 2.522 mmol) and DCC (520 mg, 2.522 mmol) were dissolved (no obvious dissolution) in $CH_2Cl_2$ (11.5 ml, to make a 0.22 M solution). The reaction was allowed to mix overnight at room temperature. The crude reaction mixture was filtered through a sintered glass funnel to remove the dicyclohexylurea (DCU). The reaction was filtered "anhydrously" into a flask containing 316 mg (2.522 mmol) taurine. The filter cake was washed with 3, 5 ml volumes of $CH_2Cl_2$. After adding 316 ml $Et_3N$ (1 eq), the reaction was allowed to mix at room temperature. The reaction was allowed to mix until complete by NMR. The crude reaction mixture was purified by trituration with MeCN. The crude reaction mixture was dissolved in 14 ml $CH_2Cl_2$ (0.2 M) and 1 eq of triflic acid was added. The reaction was allowed to mix overnight at room temperature although the reaction appeared complete after mixing for only 15–20 minutes. The reaction mixture was filtered and the filter cake washed with $CH_2Cl_2$. The filter cake (the free acid) was divided into two portions. One portion (305 mg) and 0.5 eq $Zn(OH)_2$ were dissolved in 5 ml $H_2O$ and allowed to mix for 1 hour and then it was concentrated by lyophilization to give 340 mg as a white solid (66% based on starting N-(CBZ)-β-alanine). The other portion was purified and characterized as the free acid (190 mg). NMR data were obtained on both the free acid and the Zn salt, the Zn salt being the more pure.

The $^1H$ NMR spectral data were as follows:

| Signal | $D_2O$ solvent |
| --- | --- |
| a | 2.99 (t, J = 12.8 Hz, 2H) |
| b | 3.48 (t, J = 12.8 Hz, 2H) |
| c | not seen due to hydrogen bonding |
| d | 2.38 (t, J = 12.4 HZ, 2H) |
| e | 3.35 (m, 2H) |
| f | not seen due to hydrogen bonding |
| g | 5.07 (m, 4H) |

The $^{13}C$ NMR spectral data were as follows:

| Signal | DMSO solvent |
| --- | --- |
| 1 | 51.1 |
| 2 | 36.1 |
| 3 | 170.2 |
| 4 | 36.4 |
| 5 | 37.7 |
| 6 | 156.6 |
| 7 | 65.7 |
| 8 | 137.8 |
| 9 | 128.3 |
| 10 | 128.9 |
| 11 | 128.9 |

Method IIb

Preparation of N-Carbobenzoxy-β-alanyl-taurine (Free Acid and Zinc Salt) from N-(CBZ)-β-Alanine (Scale up)

In a three-neck 1 L flask was placed CBZ-β-alethine (48.2 g, 215.9 mmol) under $N_2$. To this was added freshly distilled methylene chloride (750 mL), followed by N-hydroxysuccinimide (24.85 g, 215.9 mmol). To the resulting suspension was added 1,3-dicyclohexylcarbodiimide (DCC, 44.54 g, 215.9 mmol). At this scale the reaction generated a noticeable exotherm, sufficient to reflux the $CH_2Cl_2$. The reaction mixture was stirred under $N_2$ for 5 hours at which point the mixture was filtered through a sintered glass buchner funnel. The filter cake was washed with $CH_2Cl_2$ (3×100 mL). To the filtrate was added taurine (27.03 g, 215.9 mmol) and triethylamine (33.1 mL, 237.5 mmol). The reaction was stirred under $N_2$ and monitored by $^1H$-NMR analysis. The reaction mixture was vacuum filtered through a buchner funnel using Whatman #542 filter paper. The filtrate was stripped to an oil using reduced pressure, then placed on high vacuum. The "oil" was triturated with acetonitrile with one drop of water to quench any unreacted DCC. The mixture was filtered and the MeCN was stripped off under reduced pressure then placed on high vacuum. The resulting oil was dissolved in water (50 mL). A curdy white precipitate formed, more water (150 mL) was added and the resulting solid was filtered off. In the filtrate an oil precipitated out of solution. $^1H$-NMR spectra were obtained to determine the location of product. The product was in the aqueous layer as expected. The aqueous phase containing the product was then eluted through a H+ ion exchange column. Fractions (225 mL) were collected and spotted on TLC. The desired product was found in fractions 2–7. These fractions were combined and the water removed under reduced pressure. To the resulting oil was added MeCN (1 L) and the solution was stirred. The remaining water was removed by azeotropic distillation with the MeCN. The resulting solid was collected by vacuum filtration and washed with MeCN. The solid was vacuum dried in a 1 L round bottom flask then transferred to a tared 4 oz. amber bottle. Final package weight was 38.89 g (117.7 mmol, 54.5% yield). The zinc salt was prepared by treatment with $Zn(OH)_2$ in $H_2O$, followed by lyophilization. The spectral data for the product matched exactly a standard sample of N-carbobenzoxy-b-alanyl-taurine zinc salt.

Example II

Synthesis off β-Alanyl-Taurine (Free Acid and Zinc Salt)

N-carbobenzoxy-β-alanyl-taurine (1.00 g, 3.4 mmol) was slurried in 23 ml glacial AcOH. To the mixture was added 3.4 mL HBr in AcOH (30 wt %) to result in a clear solution. The reaction was heated to 40/C and allowed to mix overnight. The product precipitated out of solution and acetonitrile was added to force the precipitation. The mixture was filtered, the filter cake washed and the product collected. The crude Br salt was loaded onto an ion exchange column (Dowex AG1-XB8). The column was eluted with $H_2O$. The product cut was collected and lyophilized to give 583 mg of β-alanyl-taurine (87.3%). The zinc salt was prepared by treatment with $Zn(OH)_2$ in $H_2O$, followed by lyophilization.

The $^1H$ NMR spectral data were as follows:

| Signal | $D_2O$ solvent |
| --- | --- |
| a | 3.09 (t, J = 12 Hz, 2H) |
| b | 3.59 (t, J = 12 Hz, 2H) |
| c | not seen due to hydrogen bonding |
| d | 2.66 (t, J = 12 Hz, 2H) |
| e | 3.25 (t, J = 12 Hz, 2H) |

The $^{13}C$ NMR spectral data were as follows:

| Signal | DMSO solvent |
| --- | --- |
| 1 | 50.8 |
| 2 | 36.2 |

-continued

| Signal | DMSO solvent |
|--------|--------------|
| 3 | 169.6 |
| 4 | 33.1 |
| 5 | 36.2 |

For comparison, beta-alanyl-taurine zinc salt prepared using the method of Knight et al, Cancer Research 54:5623 (1994) gave the following $^1$H NMR spectra:

| Signal | D$_2$O solvent |
|--------|----------------|
| a | 2.93 (t, J = 12 Hz, 2H) |
| b | 3.42 (t, J = 12 Hz, 2H) |
| c | not seen due to hydrogen bonding |
| d | 2.50 (t, J = 12 Hz, 2H) |
| e | 3.10 (t, J = 12 Hz, 2H) |

Example III

Preparation of N-Carbobenzoxy-b-Alanyl-Ethanolamine Phosphate (Free Acid and Zinc Salt) from N-(CBZ)-β-Alanine N-(CBZ)-b-alanine (274 mg, 1.23 mmol), N-hydroxysuccinimide (141 mg, 1.23 mmol) and dicyclohexylurea (DCC, 253 mg, 1.23 mmol) were dissolved in tetrahydrofuran (THF, 4.1 mL). The reaction was allowed to mix at room temperature overnight before being filtered to remove the dicyclohexylurea (DCU). To the filtrate, a solution of 2-aminoethyl phosphate (1.23 mmol) in H$_2$O (0.5 ml) was added. To the reaction mixture was added 2.1 molar equivalents of triethylamine. The reaction was allowed to mix for three days before the THR was removed under vacuum. The remaining aqueous phase was filtered and loaded onto a prepared ion exchange column (Dowex AG 50W-X8). The column was eluted with water. The product fractions were collected and lyophilized. The crude solid (260 mg) was treated wiTh1.0 molar equivalents of Zn(OH)$_2$ in H$_2$O to make the salt. The crude solid (after lyophilization) was triturated with acetronile and collected (50 mg).

Example IV

Synthesis of N-Carbobenzoxy-β-Alanyl-Aminoethylphosphonic Acid (Free Acid and Zinc Salt) from N-(CBZ)-β-Alanine N-(CBZ)-β-alanine (301 mg, 1.35 mmol), N-hydroxysuccinimide (155 mg, 1.35 mmol) and dicyclohexylurea (DCC, 278 mg, 1.35 mmol) were dissolved in tetrahydrofuran (THF, 4.5 ml). The reaction was allowed to mix at room temperature overnight before being filtered to remove the dicyclohexylurea (DCU). To the filtrate, a solution of 2-aminoethylphosphonic acid (1.35 mmol) in H$_2$O (0.5 ml) was added. To the reaction mixture was added 2.1 molar equivalents of triethylamine. The reaction was allowed to mix for three days before the THF was removed under vacuum. The remaining aqueous phase was filtered and loaded onto a prepared ion exchange column (Dowex AG 50W-X8). The column was eluted with water. The product fractions were collected and lyophilized. The crude solid (270 mg) was treated wiTh1.0 molar equivalents of Zn(OH)$_2$ in H$_2$O to make the salt. The crude solid (after lyophilization) was triturated with acetonitrile and collected (50 mg).

Example V

Method of Synthesizing β-Alethine

The synthesis of beta-alethine is a 5 step process consisting of three synthetic steps and two purification steps. Below is a brief description of each step.

Step 1 is the formation of the activated ester from N-CBZ-beta-alanine (compound 1). The N-CBZ-/beta-alanine activated ester (compound 2) is not isolated instead it is taken directly to step 2 in solution.

Step 2 is the coupling of the activated ester (from step 1) to cystamine dihydrochloride. The product compound is N,N'-bis-CBZ-b alethine (Compound 3).

Step 3 is the removal of the CBZ groups from N,N'-bis-CBZ-beta-alethine using HBR/AcOH [spell out]. The resulting compound is beta-alethine TM-2HBR (beta-alethine TM hydrobromide salt) (compound 4).

Step 4 uses ion-exchange chromatography to exchange the Br ion on beta-alethine TM-2HBR for a Cl ion and to remove non-ionic organic impurities. The resulting compound is beta-alethine TM (compound 5)

Step 5 is a precipitation of the beta-alethine TM using acetone and water. The resulting compound is the purified final product (compound 5).

Detailed Description of the Process

Step 1

N-CBZ-/beta-alanine (Compound 1) (P/N 0665) is slurried in anhydrous dichloromethane (P/N 0374) to make a 0.3M solution. To the slurry is added 1 molar equivalent N-hydroxysuccinimide (P/N 0696) and 1 molar equivalent dicyclohexylcarbodiimide (DCC, P/N 1267). The mixture is stirred at room temperature for at least 6 hours and no more than 68 hours. The reaction mixture now contains dicyctohexylurea, a bi product of the reaction, and is a mixture of solids and liquid.

Step 2

The crude mixture is filtered under an argon blanket using a sintered glass funnel. The liquid is filtered into a reaction vessel containing 0.4 molar equivalents of the cystamine dihydrochloride (P/N 0821). The solid dicyclohexylurea (DCU) is washed with 3×200 mL portions of anhydrous dichloromethane. Triethylamine (P/N 0247), 0.8 molar equivalents, is added and the reaction mixture is allowed to stir for at least 12 but no more than 68 hours. The reaction is now a mixture of liquid and solids.

To this crude mixture is added enough HPLC grade acetone (P/N 0828) to equal the amount of dichloromethane present. The mixture is then stirred for 2 to 4 hours before being filtered through a Buchner funnel fitted with Whatman's #541 filter paper (P/N 0286). The solid N,N'-bis-CBZ-beta-alethine (Compound 3) (P/N 1277) is then washed with 3,200 mL portions of I-IPLC grade acetone. The solid is collected and dried in a vacuum oven at 40° C.

The crude solid, N,N'-CBZ-beta-alethine, is slurried in acetonitrile (P/N 2017) to make a 0.3M solution. The mixture is heated to 50° C. to dissolve the solids. Once the solids have dissolved, deionized water (P/N 1793) in an amount sufficient to make 0.15M, is slowly added and the mixture is allowed to cool to room temperature. The purified N,N'-CBZ-beta-alethine (P/N 1286) is filtered off using an 18.5 cm Buchner funnel fitted with Whatman's #541 filter paper. The purified solids are washed with deionized water, collected, and dried in a vacuum oven at 40° C.

References: 1) Cancer Research, 1994, 54, 5636–5642. 2) Cancer Research, 1994, 54, 5623–5635. 3) World Pat. WO 92/00955. 4) HCR notebooks 1576-1, 1576-7, 1576-15, 1576-28, 1576-42, 1576-118, 159b-83, 159b-105, 159b-119, 159b-139, 1613-150, 1613-154, 1649-39, 1714-88, 1714-102.

Step 3

The purified N,N'-bis-CBZ-beta-alethine is slurried in enough glacial acetic acid (PN 0503) to make a 0.15 M solution. The HBR/AcOH mixture (P/N 1282) is then added and all solids dissolve. The reaction is allowed to stir overnight at room temperature (for at least 15 but no more than 68 hours) during which time the reaction product precipitates out of solution. After mixing enough HPLC grade acetone is added to the reaction mixture to equal one half the amount of glacial acetic acid. The mixture is allowed to mix an additional 2 to 4 hours before being filtered through a Buchner funnel fitted with Whatman's #541 filter paper. The solid beta-alethine ™ hydrobromide salt (Compound 4) (P/N 1287) is then washed with 3×150 mL volumes of HPLC grade acetone. The solids are collected and dried in a vacuum oven at 40° C.

References: 1) Cancer Research, 1994, 54, 5636–5642. 2) Cancer Research, 1994, 54, 5623–5635. 3) World Patent WO 92/00955. 4) HCR notebooks 1576-6, 1576-17, 1576-25, 1576-25, 1576-38, 1576-86, 1576-88, 1576-89, 1576-117, 1576-153, 159b-103, 159b-121, 159b-141, 1613-153, 1649-40, 1714-100.

Step 4

A 4"×3' ion exchange column is slurry packed with BioRad Dowex AG 1-X8 chloride form anion-exchange resign (P/N 1408). The slurry solution used is a 1M solution of KCl (P/N 1283) in deionized water (P/N 1793). The column is washed with 3 column volumes of the 1M KCl solution followed by 3 column volumes of deionized water. The hydrobromide salt of beta-alethine TM (Compound 4) is dissolved in deionized water and filtered through a sintered glass funnel to remove any particulate matter. The filtrate is loaded directly onto the ion exchange column and dispersed. The column is eluted with deionized water and 100 mL fractions are collected. Fractions are spotted on a silica gel plate and tested under a UV lamp. The fractions that contain the product (beta-alethine TM) (Compound 5) quench under a UV lamp. Product containing fractions are collected, frozen and lyophilized.

The residual solid is dissolved in 1.5 mL water for injection (P/N 0079) per gram of solid. To the aqueous solution is added 10% wt/wt activated carbon (P/N 0472). The slurry is mixed for at least minutes before being filtered. To this solution is added a 10 fold excess of HPLC grade acetone. The mixture is allowed to mix for 1 to 4 hours at room temperature before being filtered through a Buchner funnel fitted with Whatman's #541 filter paper. The solid beta-alethine ™ is then washed with three, 150 mL portions of HPLC grade acetone. The solid product is collected and dried in a vacuum oven at 40° C. until a constant weight is achieved.

beta-aletheine, the reduced form of beta-alethine, is unstable in air and aqueous solutions (The Merck Index, $9^{th}$ edition (#221), Merck & Co., Rahway, N.J., U.S.A.).

References: 1) Cancer Research, 1994, 54, 5636–5642. 2) Cancer Research, 1994, 54, 5623–5635. 3) World Patent WO 92/00955. 4) HCR notebooks 1576-6, 1576-17, 1576-25, 1576-25, 1576-38, 1576-86, 1576-88, 1576-89, 1576-117, 1576-153, 159b-103, 159b-121, 159b-141, 1613-153, 1649-40, 1714-100.

Example VI

Beta-alethine Effects on Cytokine Production from T-cells

To observe the effect of Beta-alethine and Taurox-SB on cytokine production, PBMCs were cultured 6 hours with or without PMA/ionomycin in the presence or absence of beta-alethine. Expression of each panel of cytokine mRNAs was determined by RNase protection assay. Standards were presented in lane 1; L32 and GAPDH were included as controls.

RNase Protection Assay: PBMC ($1\times10^7$ cells) were cultured in 10 mL RPMI/10% FBS for 6 hours with or without PMA/ionomycin in the presence or absence of beta-alethine at concentrations of 27 nM, 2.7 mM or 20 mM. RNA was extracted with acid guanidinium thiocyanate-phenol-chloroform using the RNA Isolation Kit from Pharmingen. RNase protection was performed using RiboQuant™ from Pharmingen and a human cytokine multi-probe template.

Figure 1:
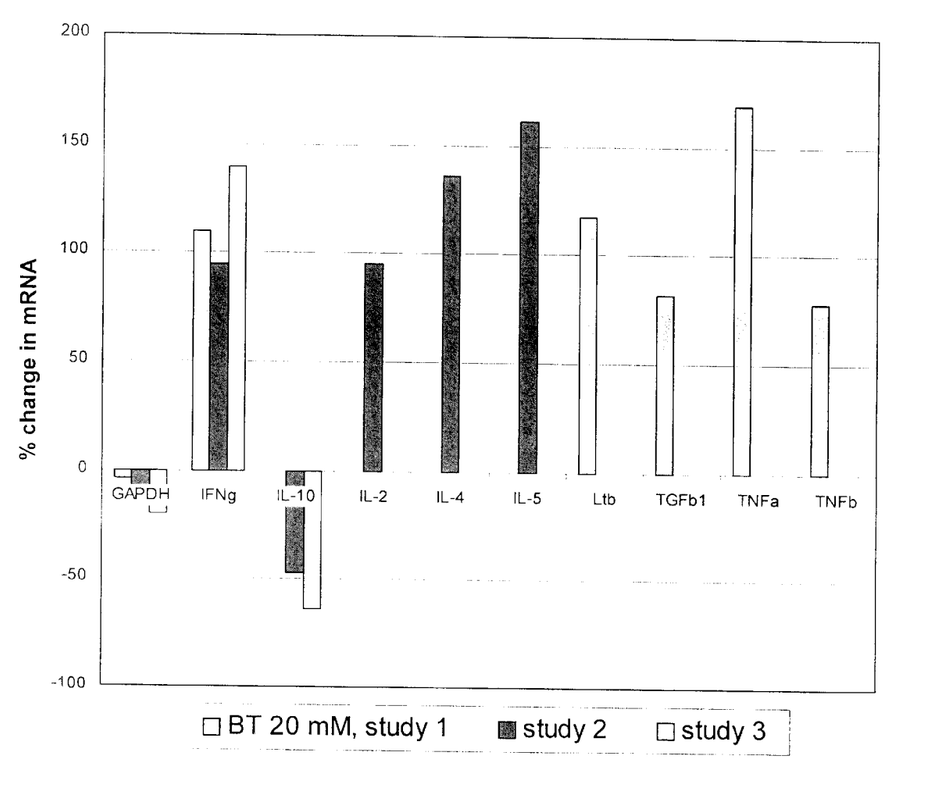
FIG. 1 The effect of 20 mM beta-alethine on messenger RNA for IFN-gamma, TNF alpha, TNF beta, IL-2, IL-4, IL-5, IL-10, and Lymphotoxin-beta (LTb).

The results presented in Table 1 and FIG. 1 show that 20 mM BT caused a dramatic increase in messenger RNA for the most important Th1 cytokine IFN-gamma, as well as the other Th1 cytokines IL-2, TNF alpha, TNF beta and Lymphotoxin from unstimulated human T cells. At the same time, BT significantly depressed the production of dominant Th2 cytokine IL-10, which is required to maintain a sustained Th2 response.

In cells that are already overly or highly stimulated by PMA and ionomycin, the compounds do not cause a coordinated increase in Th1 cytokines rather their action modulates the immune response and decreases many of the Th1 and other cytokines being produced at elevated levels by the overly stimulated cells. Notice in the stimulated T cell model that IFN-gamma, IL-2, Lymphotoxin Beta, and the chemokines MIP-1a, MIP-1b and RANTES are depressed. The present invention is thus a set of compounds that modulate the immune response causing a coordinated increase or decrease in various cytokines and other signaling molecules to obtain a desired effect.

TABLE 1

Beta-alethine Effects on Cytokine mRNA from Unstimulated T cells
% Change
BETATHINE, no stimulation

| Genes | BT 27 nM | BT 2.7 uM | BT 20 mM | BT 20 mM | BT 20 mM | BT 20 mM |
|---|---|---|---|---|---|---|
| GAPDH | −10.95 | −4.78 | −4.03 | −10.53 | −19.63 | 0.80 |
| IFNg | 21.11 | 20.17 | 109.71 | 94.74 | 139.51 | |
| IL-10 | | | | −47.42 | −63.49 | |
| IL-13 | | | | 83.76 | | |
| IL-15 | | | | 4.88 | | |
| IL-1a | | | | | 9.07 | |
| IL-1b | | | | | 60.09 | |
| IL-1Ra | | | | | 30.84 | |

TABLE 1-continued

Beta-alethine Effects on Cytokine mRNA from Unstimulated T cells
% Change
BETATHINE, no stimulation

| Genes | BT 27 nM | BT 2.7 uM | BT 20 mM | BT 20 mM | BT 20 mM | BT 20 mM |
|---|---|---|---|---|---|---|
| IL-2 | | | | 95.02 | | |
| IL-4 | | | | 135.82 | | |
| IL-5 | | | | 161.15 | | |
| IL-8 | | | | | | 10.65 |
| IL-9 | | | | 22.86 | | |
| IL-10 | | | | | | −73.71 |
| LTb | 27.48 | 25.70 | 117.13 | | | |
| LTN* | | | | | | 58.25 |
| MIP-1 alpha | | | | | | 25.98 |
| MIP-1 beta | | | | | | −4.79 |
| RANTES | | | | | | −2.09 |
| TGFb1 | 26.69 | 42.15 | 82.08 | | | |
| TNFa | 10.04 | 24.94 | 168.85 | | | |
| TNFb | 42.88 | 220.87 | 77.91 | | | |

TABLE 2

Beta-alethine Effects on Cytokine mRNA from Stimulated T cells
BETATHINE, WITH STIMULATION

| Genes | 27 nM | 2.7 uM | 20 mM | 20 mM | 20 mM | 20 mM |
|---|---|---|---|---|---|---|
| GAPDH | −15.76 | −5.57 | 71.70 | 8.48 | −1.45 | −2.38 |
| IFNg | −15.41 | −16.91 | 31.87 | −53.10 | −31.77 | |
| IL-10 | | | | −20.39 | 44.77 | |
| IL-13 | | | | −52.30 | | |
| IL-15 | | | | −22.71 | | |
| IL-1a | | | | | 36.09 | |
| IL-1b | | | | | 192.83 | |
| IL-1Ra | | | | | −81.63 | |
| IL-2 | | | | −54.53 | | |
| IL-4 | | | | 18.15 | | |
| IL-5 | | | | 106.44 | | |
| IL-8 | | | | | | −9.46 |
| IL-9 | | | | −18.21 | | |
| IL-10 | | | | | | −13.39 |
| LTb | 17.67 | 3.82 | 23.86 | | | |
| LTN* | | | | | | −52.59 |
| MIP-1 alpha | | | | | | −54.64 |
| MIP-1 beta | | | | | | −61.85 |
| RANTES | | | | | | −53.10 |
| TGFb1 | −27.39 | −7.75 | 83.57 | | | |
| TNFa | −12.54 | 22.73 | 261.99 | | | |
| TNFb | −8.31 | 15.25 | 23.65 | | | |

*LTN = lymphotactin

Monocyte expression of chemokines was also assessed in beta-alethine-treated cells (Table 3). While IP-10 expression was decreased by beta-alethine, the levels of the chemoattractants MIP-1a and IL-8 were increased slightly. Bacterial infections are contained by an inflammatory response. MIP-1a recruits macrophages, T cells and eosinophils to the infection site, and IL-8 recruits neutrophils. Therefore both of these chemokines are important in fighting pathogen-induced infections.

TABLE 3

Beta-alethine effects on Monocyte Chemokine Message levels.*

| Cytokine | Media | Media + beta-alethine |
|---|---|---|
| MIP-1 alpha | 721,770 | 909,291 |
| MIP-1 beta | 582,639 | 554,709 |
| IP-10 | 209,997 | 55,214 |
| IL-8 | 10,497,856 | 11,615,894 |

*Data from RPA were quantified by phosphorimaging and normalized on the basis of the housekeeping gene L32. Beta-alethine was used at 20 mM.

Example VII

The Effect of Taurox-SB on mRNA for TNF Alpha and Other Cytokines

The effect of Taurox-SB on mRNA for TNF alpha and other cytokines was determined at two different concentrations, 1.4 μm and 1.4 mM. PBMCs were incubated with Taurox-SB for 6 hours and message levels determined by RPA. Taurox-SB at both 1.4 μm and 1.4 mM increased TNF alpha, Lymphotoxin and IFN-gamma message, while decreasing that for TGF beta at the 1.4 mM concentration (Table 4). Therefore, BT and Taurox-SB exhibit similar effects on cytokine mRNA levels.

TABLE 4

Taurox-SB Effects on Cytokine Message.*

| | TAUROX-SB no stimulation | | | TAUROX-SB with stimulation | | |
|---|---|---|---|---|---|---|
| Genes | 14 nM | 1.4 uM | 1.4 mM | 14 nM | 1.4 uM | 1.4 mM |
| TNFb | 62.96 | 311.16 | 373.82 | 22.72 | 4.18 | 20.95 |
| Ltb | 29.83 | 21.09 | 85.61 | 12.29 | 2.92 | 234.28 |
| TNFa | 2.10 | 21.27 | 461.93 | −15.96 | 48.67 | −100.00 |
| IFNg | 21.53 | 16.76 | 388.08 | −32.73 | −9.85 | −64.90 |
| TGFb1 | 17.51 | 29.61 | 36.89 | −10.25 | −0.09 | −25.88 |
| GAPDH | −20.94 | −8.16 | 4.96 | −8.10 | 4.88 | −38.75 |

Example VIII

Surface TNF Alpha Regulation on T Cells by Beta-alethine or Taurox-SB

Methods:

Compounds: N-acetyl-L-cysteine (NAC), phorbol 12-myristate 13-acetate (PMA), Ionomycin, and HEPES were purchased from Sigma (St. Louis, Mo.). BT was synthesized and analyzed for purity by Hauser (Boulder, Colo.) and obtained from Dovetail Technologies (College Park, Md.). RPMI 1640 medium, penicillin, and streptomycin was purchased from Gibco BRL (Bethesda, Md.). Fetal Bovine Serum (FBS) was purchased from Gemini-Bio-Products, Inc (Calabasas, Calif.).

Relative shifts in mean fluorescent intensity (MFI) and percent gated were compared to either a medium only or stimulation (Ionomycin plus PMA) only controls.

Purification and Stimulation of cells: Peripheral blood mononuclear cells (PBMC) were purified from the blood of healthy human donors and separated over Ficoll-Histopaque 1077 (Sigma) for 30 minutes at 900 g. Human peripheral blood lymphocytes (PBL) and peripheral blood monocytes (PBM) were donated by Walter Reed Army Institute of Research and were obtained through counter flow centrifugal elutriation. 106 cells were cultured in 12×75 mM tissue culture tubes in 1 mL of media consisting of RPMI 1640, 20% FBS, 20 mM HEPES, 50 mg/mL streptomycin, and 50 Units/mL penicillin. The cells were incubated for 16 hours at 37° C. with or without stimulation by 1 microMol/L ionomycin and 10 ng/mL $PMA^2$ in the presence or absence of beta-alethine or NAC.

Surface TNF Alpha and TNF Alpha Receptor Labeling.

Cells were labeled with (1) either fluorescence isothiocyanate (FITC)-conjugated mouse anti-human TNF alpha monoclonal IgG (Serotec, Raleigh, N.C.) or control IgG1 (Becton Dickinson, San Jose, Calif.), or with (2) anti-TNF receptor I (TNF-R I) antibody (Bio Whittaker, Walkersville, Md.) or control IgG2a (Becton Dickinson). The labeled cells were than incubated with FITC-conjugated goat anti-mouse IgG (Sigma) for 30 minutes at 4° C. in FACS buffer (0.5% bovine serum albumin, 10 mM sodium azide in phosphate buffered saline). Phycoerythrin (PE)-conjugated mouse anti-human CD3 monoclonal IgG (Biosource, Sunnyvale, Calif.) or PE-conjugated mouse anti-human CD14 (Sigma) was used for double labeling. The cells were then washed twice with 2 mL FACS buffer and expression of surface TNF alpha was measured on a FACS (Fluorescent Activated Cell Sorter) Calibur (Becton Dickinson, San Jose, Calif.) after gating on CD3+ cells or CD14+ cells. Results are expressed as either one parameter histograms or mean fluorescence intensity (MFI).

Measurement of soluble TNF alpha. Supernatants from cells prepared as described above were collected, and secreted (i.e., soluble) TNF alpha was measured by ELISA using a matched pair antibody system from R&D Systems (Minneapolis, Minn.). The range of the standard curve was from 15.6–1,000 pg/mL with an assay sensitivity of 5 pg/mL.

RNase Protection Assay: PBMC (1×107 cells) were cultured in 10 mL RPMI/10% FBS for 6 hours with or without PMA/ionomycin in the presence or absence of beta-alethine at concentrations of 27 nM, 2.7 mM or 20 mM. RNA was extracted with acid guanidinium thiocyanate-phenol-chloroform using the RNA Isolation Kit from Pharmingen. RNase protection was performed using RiboQuant™ from Pharmingen and human cytokine multi-probe templates.

Results

Experiment 1

Beta-alethine Increases Surface TNF Alpha Expression by Human T cells

Unstimulated and PMA/ionomycin treated-T cells were incubated with and without BT, the well-characterized thiol antioxidant NAC, or a combination of BT and NAC. All drugs were used at a concentration of 20 mM. Table 5. In the absence of stimulation, human T cells from PBMCs treated with BT alone exhibited an inconsistent upregulation of surface TNF alpha between donors. The increase in surface TNF alpha in unstimulated T cells treated with BT alone for a single donor showed a three-fold increase over control levels at 15 hours post-exposure (from 25 to 75) about a two-fold increase (from 25 to 100) at forty hours.

Unstimulated T cells from three donors incubated with NAC alone for 16 hours also exhibited an inconsistent upregulation of surface TNF alpha which was variable from donor to donor. By contrast, the combination of 20 mM NAC and 20 mM BT consistently increased surface TNF alpha expression on a small subpopulation of unstimulated T cells. Table 5.

TABLE 5

Effects of BT and NAC on TNF alpha in T Cells

| Donor/Date | Without BT | With BT | Change |
| --- | --- | --- | --- |
| Stimulation | | | |
| PBL 9/17/97 | 172.63 | 435.04 | 152.007 |
| PBL 3/26/98 | 19.79 | 25.17 | 27.185 |
| TD 9/24/97 | 248.39 | 508.43 | 104.690 |
| TD 10/8/97 | 68.74 | 292.59 | 325.647 |
| TD 10/9/97 48 hrs | 79.56 | 146.81 | 84.527 |
| TD 1/20/98 | 113.26 | 164.48 | 45.223 |
| TD 3/31/98 | 50.32 | 83.65 | 66.236 |
| BI 11/5/97 | 82.91 | 123.87 | 49.403 |
| BI 2/25/98 1 ng PMA | 45.83 | 133.13 | 190.487 |
| BI 1/23/98 | 15.16 | 25.93 | 71.042 |
| TM 2/5/98 | 46.54 | 48.53 | 4.276 |
| TM 2/17/98 | 62.61 | 105.59 | 68.647 |
| TM 2/25/98 1 ng PMA | 13.79 | 25.41 | 84.264 |
| NAC | | | |
| PBL 3/26/98 | 24.7 | 25.81 | 4.494 |
| BI 2/25/98 | 6.96 | 16.35 | 134.914 |
| TM 2/5/98 | 17.49 | 46.79 | 167.524 |
| TM 2/17/98 | 6.34 | 13.48 | 112.618 |
| TM 2/25/98 | 6.68 | 10.1 | 51.198 |
| NAC + Stimulation | | | |
| PBL 3/26/98 | 25.32 | 26.35 | 4.068 |
| TD 3/31/98 | 31.12 | 44.28 | 42.288 |
| BI 11/5/97 | 95.45 | 188.27 | 97.245 |
| BI 2/25/98 1 ng PMA | 11.31 | 18.66 | 64.987 |
| BI 1/23/98 | 53.48 | 63.22 | 18.212 |
| TM 2/5/98 | 17.39 | 40.98 | 135.653 |
| TM 2/17/98 | 12.59 | 20.7 | 64.416 |
| TM 2/25/98 1 ng PMA | 12.76 | 16.46 | 28.997 |

The change reflects a % positive or % negative change in with BT/without BT
The numbers used are representative of overal MFI, not gating on positive peak
All values are based on 20 mM BT and/or 20 mM NAC
Stimulation is 1 micromolar Ionomycin and 10 ng/ml PMA unless indicated othewise PMA/ionomycin stimulation of T cells produced an increase in surface TNF alpha expression[23] over the levels observed in unstimulated controls. Although NAC has been reported to further increase expression of surface TNF alpha[19] in stimulated cells. Any increase in surface TNF alpha caused by NAC in stimulated PBMC cultures was small and highly variable between the three donors. Some donor cells actually exhibited a decrease in surface TNF alpha expression in response to NAC, relative to stimulation with PMA/ionomycin alone.

BT, however, dramatically elevated surface TNF alpha expression in stimulated cells above levels induced by PMA/ionomycin, and the elevation was consistent and reproducible between donors. BT treatment did not alter binding of the FITC-conjugated isotype control. This means that the changes in TNF alpha are not an artifact caused by the anti-TNF alpha antibody binding to Fc receptor on the cell surface. BT also induced upregulation of surface TNF alpha expression on a panel of human T-cell lines (data not shown). Surface TNF alpha expression by stimulated T cells is consistently enhanced by BT treatment. Table 5 (stimulated T cells).

The combination of BT/NAC in stimulated T cells was not synergistic for stimulated monocytes, instead the Mean Fluoresent Intensity (MFI) of these cells was mid-way between those of cells treated with NAC or beta-alethine individually.

Experiment 2

Beta-alethine Increases Surface TNF Alpha Expression by Human Monocytes

The effect of NAC and BT, alone or in combination, on surface TNF alpha expression by stimulated or unstimulated monocytes (prepared from PBM) was examined. All drugs were used at a concentration of 20 mM. As observed for human T cells, surface TNF alpha was not upregulated on unstimulated monocytes by either NAC or BT alone, however, the combination of NAC/BT significantly increased surface TNF alpha expression. Table 6. While only a small proportion of T cells from each donor were responsive to the combination NAC/BT, the effect on surface TNF alpha expression in monocytes was significant. In some cases the entire population of monocytes showed elevated surface TNF alpha expression.

In stimulated monocytes, BT alone induced significant surface TNF alpha expression. This contrasted with the relative ineffectiveness of NAC alone. The BT and NAC combination produced a moderate increase; mean fluorescence channel of these cells was midway between those of cells treated with NAC or BT, individually.

TABLE 6

Effects of BT on TNF alpha from Monocytes

| Monocytes Donor/Date | Without BT | With BT | |
|---|---|---|---|
| Media | | | |
| PBM 3/19/98 | 69.47 | 124.26 | 78.86857636 |
| TD 9/24/97 | 18.86 | 10.53 | −44.16755037 |
| TD 10/8/97 | 20.29 | 24.06 | 18.58058157 |
| TD 10/9/97 48 hrs | 14.21 | 14.22 | 0.070372977 |
| Stimulation | | | |
| PBM 3/19/98 | 64.03 | 71.42 | 11.54146494 |
| TD 9/24/97 | 57.9 | 202.15 | 249.1364421 |
| TD 10/8/97 | 88.52 | 41.97 | −52.58698599 |
| TD 10/9/97 48 hrs | 36.84 | 34.59 | −6.107491857 |
| TD 3/31/1998 | 63.31 | 143.51 | 126.6782499 |
| BI 11/5/97 | 38.47 | 87.59 | 127.6839095 |

TABLE 7

Effect of BT/NAC on TNF alpha from Monocytes

| Monocytes Donor/Date | Without BT | With BT | |
|---|---|---|---|
| NAC | | | |
| PBM 3/19/98 | 78.78 | 77.74 | −1.320132013 |

TABLE 7-continued

Effect of BT/NAC on TNF alpha from Monocytes

| Monocytes Donor/Date | Without BT | With BT | |
|---|---|---|---|
| NAC + Stimulation | | | |
| PBM 3/19/98 | 71.42 | 76.5 | 7.112853542 |
| TD 3/31/1998 | 31.12 | 44.28 | 42.28791774 |
| BI 1/5/97 | 95.45 | 188.27 | 97.2446307 |

The results set forth in above show that both stimulated T cells and monocytes respond to BT with a consistent, significant and reproducible increase in surface TNF alpha expression. Further, the increase of surface TNF alpha expression induced by BT is more reproducible and more potent than that induced by exposure to NAC. Table 7 (monocytes).

Experiment 3

The Effects of Beta-alethine on T cells are Dose and Time Dependent

T cells prepared from PBMC were incubated for 16 hours at 37° C. with PMA/ionomycin and beta-alethine at concentrations of 8.7 mM to 20 mM. Under these conditions, surface TNF alpha expression was increased in a dose dependent fashion.

In this experiment, the percentage of T cells expressing high levels of surface TNF alpha was determined. As Table 8 shows, increasing doses of BT are correlated with increasing the percentage of T cells that express high levels of surface TNF alpha.

TABLE 8

Dose/Response

| Dose (mM) | MFI ± SD | % Positive ± SD |
|---|---|---|
| .0085 | 59.84 ± 4.08 | 4.96 ± .41 |
| .027 | 63.49 ± .28 | 5.18 ± 1.73 |
| .085 | 74.18 ± 7.98 | 8.4 ± .5 |
| .27 | 71.17 ± .77 | 7.33 ± .38 |
| .85 | 81.93 ± 6.33 | 9.38 ± 1.57 |
| 2.7 | 94.52 ± 1.83 | 10.86 ± .92 |
| 20 | 127.37 ± 12.5 | 24.25 ± 6.25 |

The time dependence of the BT-induced increase in surface TNF alpha expression was quantified from 6 hours through 68 hours in culture in the absence or presence of PMA/ionomycin, with or without 20 mM BT and/or 20 mM NAC. (Table 9) Unstimulated T cells did not exhibit significantly enhanced surface TNF alpha in response to NAC at any time point examined. By contrast, BT treatment increased surface TNF alpha expression in unstimulated cells for 40 hours. This increase was maintained through 68 hours in cells treated with the combination, although at slightly lower levels.

TABLE 9

Time Course

| Time Hours | Control | NAC 20 mM | BT 2.7 mM | BT 20 | BT+ NAC | Pma/ iono | NAC 20 mM | BT 2.7 mM | BT 20 mM | BT+ NAC |
|---|---|---|---|---|---|---|---|---|---|---|
| 6 | 20 | 20 | 22 | 32 | 33 | 125 | 82 | 149 | 112 | 108 |
| 16 | 42 | 33 | 42 | 76 | 68 | 109 | 93 | 179 | 220 | 178 |
| 24 | 38 | 39 | 47 | 67 | 101 | 121 | 101 | 208 | 226 | 208 |
| 42 | 50 | 56 | 79 | 101 | 81 | 135 | 113 | 120 | 247 | 120 |
| 68 | 38 | 47 | 30 | 41 | 77 | 120 | 80 | 64 | 174 | 63 |

BT was by far the most efficient surface TNF alpha-stimulating agent in PMA/ionomycin-stimulated cells, inducing surface TNF alpha upregulation and sustaining the increased levels of expression for over 50 hours. The BT/NAC combination greatly enhanced surface TNF alpha expression for the first 20 hours, however the response in this donor's cells dropped off quickly thereafter.

Experiment 4

Beta-alethine-induced Upregulation TNF-R I

TNF receptor 1 (TNF-RI) is poorly expressed on the surface of activated T cells.[24] The ability of BT to modulate the expression of this receptor on PBMCs was therefore examined over time. Treatment of stimulated T cells with 20 mM beta-alethine dramatically increased the level of expression of TNF-R I by T cells (Table 10). The high mean flourescent channels indicate significantly elevated TNF-R I expression relative to PMA/ionomycin alone by over 50% of the T-cell population. This enhanced receptor expression was maintained through the entire 68 hours that the PBMCs were monitored. By contrast, BT had very little effect on TNFR-I expression in unstimulated T cells.

TABLE 10

Effect of BT on TNF Receptor I Expression

| Hours | Media | BT | PMA/ionomycin | PMA/ionomycin + BT |
|---|---|---|---|---|
| 20 | 91 | 136 | 168 | 329 |
| 45 | 103 | 109 | 201 | 548 |
| 69 | 51 | 96 | 146 | 489 |

Experiment 5

Effect of Beta-alethine on Production of Soluble TNF Alpha

In addition to upregulation of surface TNF alpha, PMA/ionomycin significantly (p<0.01) increased the production of soluble TNF alpha by human lymphocytes, relative to unstimulated cells. The addition of 20 mM NAC significantly decreased release of soluble TNF alpha from stimulated T-lymphocytes. There was donor variability in the NAC effect on soluble TNF alpha, which is consistent with the variability observed in surface TNF alpha expression.

BT significantly (p<0.05) decreased soluble TNF alpha release from stimulated T-lymphocytes, however the reduction was less than that observed with NAC. As observed in the flow cytometry experiments, there was limited variability in the donor response to BT. However, when NAC and BT are applied together, the detectable release of soluble TNF alpha from stimulated lymphocytes was effectively eliminated. NAC and BT therefore, appear to have different mechanisms of action, since inhibition of shedding is not like to be the sole mechanism for BT-induced upregulation of surface TNF alpha.

The combination of NAC and BT has clinical significance for treating diseases associated with an over production of soluble TNF alpha, such as anaphalactic shock and rheumatoid arthritis.

TABLE 11

BT/NAC Combination Blocks Soluble TNF

| Treatment | Media | | PMA/ionomycin | |
|---|---|---|---|---|
| Control | 2 | ± 0 | 572 | ± 32.6 |
| NAC | 15 | ± 15 | 129 | ± 102 |
| BT | 29 | ± 21 | 374 | ± 20 |
| NAC + BT | 26.5 | ± 26.5 | 2 | ± 0 |

Experiment 6

Beta-alethine Increases TNF Alpha Message

T cells (PBMCs) were treated for 6 hours with or without stimulation by PMA/ionomycin and varying concentrations of BT ranging from 27 nm to 20 mM. Messenger RNAs (mRNA) for a panel of cytokines was examined by RNase protection. Treatment of cells with 20 mM BT alone, without stimulation, lead to a pronounced increase in message for TNF alpha. This is consistent with the increased surface TNF alpha protein expression observed in BT-treated CD3+ cells as determined by flow cytometry. As anticipated, stimulation with PMA/ionomycin caused an upregulation of TNF alpha message. This upregulation was maintained in the presence of 2.7 mM BT and was even further enhanced if 20 mM BT was applied. These results show that mRNA for TNF alpha is upregulated relative to that for transforming growth factor b (TGF beta) in stimulated cells treated with 20 mM BT. TGF beta is secreted by tumors to decrease anti-tumor function of lymphocytes and macrophages. Therefore, the relatively greater increase in TNF alpha compared to TGF favors an anti-tumor immune response. Further, as discussed above, TGF beta is considered to be an immunosuppresive cytokine. When quantified by densitometry, the ratio of TNF alpha: TGF beta was 0.092 and 1.36 for cells incubated in media alone and in media +20 mM BT, respectively; and TNF alpha: TGF beta ratio was 3.61 and 7.12 for cells incubated in PMA/ionomycin alone or in PMA/ionomycin +20 mM BT, respectively. Thus, BT increased TNF alpha message relative to that for TGF beta in both unstimulated and stimulated T cells. Table 11.

Effect of Taurox-SB on TNF Alpha Expression on Human T Cells and Monocytes

Taurox-SB increases membrane TNF alpha expression on human T cells. PBMC were incubated for 16 hours with or without stimulation by PMA/ionomycin and the indicated concentration of Taurox-SB. TNF alpha expression was determined by FACS analysis, after gating on $CD3^+$ cells. Taurox-SB consistently increased TNF alpha when administered to unstimulated T cells. When Taurox-SB was administered to stimulated T cells, the MFI was increased but the mode was decreased. This means that Taurox-SB shifted a whole population of cells toward expressing more surface TNF. By contrast, BT induced a relatively smaller population of T cells to express TNF at high levels. Table 12.

TABLE 12

Taurox ™-SB Effects on TNF alpha in T cells.

| Marker | % Gated | % Total | MFI | % Total | MFI | % Total | MFI |
|---|---|---|---|---|---|---|---|
| | | Without stimulation | | | | | |
| | | Media Control | | 1.4 mM TSB | | .14 mM TSB | |
| All | 100.00 | 77.5 | 22.64 | 72.09 | 25.34 | 78.07 | 20.18 |
| | | With PMA + Ionomycin stimulation | | | | | |
| | | PMA/Ionomycin | | Stim + 1.4 mM TSB | | Stim + .14 mM TSB | |
| All | 100.00 | 80.65 | 59.12 | 88.89 | 85.04 | 85.64 | 169.68 |

As seen with BT, monocyte surface TNF alpha expression was also elevated by Taurox-SB in PMA/ionomycin-stimulated cells (Table 13). Further, in some instances Taurox-SB also increased the percentage of TNF alpha expressing monocytes in the absence of additional PMA/ionomycin stimulation.

TABLE 13

Taurox-SB Increased Monocyte TNF alpha Surface Expression.*

| Treatment | Expt. 1 | | Expt. 2 | |
|---|---|---|---|---|
| With Stimulation | MFI | % Positive | MFI | % Positive |
| Media + PMA/iono | 18.86 | 3 | 28.26 | 10 |
| Taurox-SB | 10.95 | 3 | — | — |
| PMA/iono | 57.90 | 46 | 38.47 | 12 |
| PMA/iono + Taurox-SB | 135.52 | 57 | 119.59 | 36 |

| Treatment | Expt. 3. | | Expt. 4. | |
|---|---|---|---|---|
| Without Stimulation | MFI | % Positive | MFI | % Positive |
| Media | 20.29 | 6 | 14.21 | 5 |
| Taurox-SB | 19.91 | 9 | 16.68 | — |
| PMA/iono | 88.52 | 57 | 36.84 | 44 |
| PMA/iono + Taurox-SB | 68.16 | 59 | 39.00 | 53 |

*Data from 2 of 4 representative experiments are presented as mean fluorescence intensity and the percentage of cells with fluorescence greater the isotype control peak. Taurox-SB was used at 1.4 mM.
A dash indicates not done.

Experiment 7

Beta-alethine Increases T Cell-dependent Cytotoxicity

Peripheral Blood Lymphocytes were panned with goat polyvalent anti-human immunoglobulin (Sigma) to remove B cells. The T cell-enriched population was over 80% pure as determined by staining with anti-CD3 antibody. T cells were cultured for 16 hours at 37° C. with or without PMA/ionomycin in the presence or absence of BT and/or NAC. Following culture, the T cells were fixed with 1% paraformaldehyde (PFA) for 10 minutes to exclude other cytotoxic pathways. The PFA-fixed T cells were then added at a 10:1 effector:target ratio to HL60 monocytes ($5 \times 10^4$/well) in a 96 well tissue culture plate and incubated for 24 hours. Cell viability was determined through a standard MTT (3-[4,5- Dimethylthiazol-2yl]-2,5-diphenyltetrazolium bromide; Thiazolyl blue] reduction assay.

Purified human T cells were stimulated with PMA/ionomycin in the presence or absence of various concentrations of BT and in the presence or absence of 20 mM NAC. The T cells were then fixed and added to HL60 targets at a 10:1 ratio. No cytotoxicity was observed in either unstimulated or stimulated T cells. Further, cells treated with NAC or the combination of 20 mM BT with 20 mM NAC also failed to display any increase in cytotoxic activity (Table 14).

By contrast, stimulated T cells treated with 20 mM BT alone exhibited enhanced T cell dependent cytotoxic activity toward the HL60 targets. The addition of 20 mM BT to PMA/ionomycin stimulated cells produced significantly increased levels of cytotoxicity. This activity was inhibited by the presence of neutralizing anti-TNF alpha antibodies (data not shown). Thus, the BT-induced upregulation of surface TNF alpha is of functional significance in mediating T-cell-dependent cytotoxicity.

TABLE 14

Effect of beta-alethine on T cell-Mediated Cytotoxicity

| TREATMENT | Experiment 1 | Experiment 2 |
|---|---|---|
| Media | .138 ± .006 | .215 ± .017 |
| PMA/ionomycin | .127 ± .004 | .207 ± .025 |
| PMA/ionomycin + 20 mM beta-alethine + 20 mM NAC | .141 ± .004 | ND |
| PMA/ionomycin + 20 mM NAC | .122 ± .001 | .205 ± .005 |
| PMA/ionomycin + 0.85 mM beta-alethine | ND | .191 ± .003 |
| PMA/ionomycin + 2.7 mM beta-alethine | .121 ± .001 | .193 ± .012 |
| PMA/ionomycin + 20 mM beta-alethine | .109 ± .003* | .099 ± .005* |

Results of two replicate experiments are presented as the optical density at 540 nm, plus or minus the SD. The * indicates significantly increased cytotoxicity as determined by ANOVA followed by Scheffe's F-test with p less than 0.05.

Experiment 8

Beta-alethine and Taurox-SB Enhance Cytotoxic T Lymphocyte (CTL) Activity

DBA/2 splenocytes were cultured for 6 days in either media alone, or in 2.7 mM beta-alethine, or in 0.14 mM Taurox-SB. A combination of 2,000 units/ml of IL-6 and 10 units/ml of IL-12 was used as a positive control. Measurement of cytotoxic granule formation was evaluated by assessing total cellular content of N-a-benzyloxycarbonyl-L-lysine thiobenzyl ester (BLT) esterase as described in Gajewski et al., 1995. Both BT and especially Taurox-SB were found to increase cellular BLT esterase content, indicative of enhanced CTL generation. (Table 15). The increase in generation of CTLs is consistent with the overall enhancement of cell-mediated immunity.

TABLE 15

Beta-alethine and Taurox-SB
Increase Cellular BLT Esterase Content.*

| Treatment | Expt. 1 | Expt. 2 |
| --- | --- | --- |
| Media | .099 ± .002 | .089 ± .013 |
| IL-6/IL-2 | .120 ± .001 | — |
| 2.7 mM BT | .107 ± .005 | .130 ± .006* |
| 0.14 mM Taurox-SB | .285 ± .027** | .200 ± .002* |

*Cells (1 × 10$^6$) were lysed with Triton X-100 prior to assay. Results from 2 of 3 replicate experiments are presented as mean OD405 nm SD. A dash indicates not done, and a "*" indicates significantly different from media at p < 0.05 by PLSD.

Experiment 9

Taurox-SB Increases CTL Activity

Using the DBA/2-Cloudman S-91 model, Taurox-SB was shown to effectively increase the BLT esterase activity of CTLs, which is a measure of the ability of T cells to kill other cells by necrosis. The analysis was extended to include killing of the Cloudman S-91 targets used for the CTL generation. Cloudman S-91 cells (5×104) were loaded with chloromethylfluorescein diacetate (CMFDA) and incubated for 16 hours with CTLs generated from DBA/2 splenocytes at a 10:1 effector:target ratio. Lysis was detected by leakage of the CMFDA. CTLs generated using 0.14 M Taurox-SB in addition to IL-6/IL-12 showed a significant increase in lysis from 56% to 73% relative to the IL-6/IL12 control.

The metalloproteinase TNF alpha converting enzyme (TACE), which is a Zn++-dependent endopeptidase, has been shown to cleave the 26 kDa membrane bound form of TNF alpha to yield a 17 kDa protein which is secreted as soluble TNF alpha. Metalloproteinase inhibitors are known to block this proteolytic processing in activated T cells. In order to optimize the BT-induced increase in surface TNF alpha without increasing soluble TNF alpha that could be produced by metalloproteinase cleavage, the present invention includes administering beta-alethine or Taurox-SB or other compounds of Formula I along with metalloproteinase inhibitors.

Experiment 10

T Cell Activation

CD69 Expression. CD69 expression was assessed by flow cytometry as described previously. Unlike results using beta-alethine, Taurox-SB-treated T cells exhibited increased activation as determined by enhanced expression of the activation marker CD69. Concentrations less than 1.4 mM were without effect. Representative data from Taurox-SB-treated T cells with or without PHA stimulation are shown in Table 16. CD69 is one of the earliest stimulation markers expressed on T cells upon activation (Testi et al., 1994). The cross-linking of this marker is believed to generate extracellular Ca++ influxes and activate phospholipase A2, and thus it is believed to be an integral part of the activation process (Testi et al., 1994). Upregulated CD69 may play a role in the anticancer effects of the benzyl derivative seen in vivo (Knight et al., 1994a and b).

TABLE 16

Effect of Taurox-SB on T cell CD69 Expression.*

| Treatment | MOLT-4 | MOLT-4 + PHA | HUT-78 | HUT-78 + PHA | PBMC |
| --- | --- | --- | --- | --- | --- |
| 0 | 150 | 32 | 114 | 131 | 5 |
| PHA | — | 423 | — | 385 | — |
| 1.4 mM Taurox-SB | 208 | 547 | 278 | 409 | 7 |
| 14 mM Taurox-SB | — | | — | | 11 |

*Data is expressed as MFI of 10,000 events. A dash indicates not done.
*MOLT-4, HUT-78 are T cell lines.

Experiment 11

Second Messenger Responses

As a follow-up to the observation that Taurox-SB had a CD69 stimulatory effect on T cells and because it is believed that CD69 has a role in Ca++ influx (Testi et al., 1994), we examined the Ca++ response in Taurox-SB-treated T cells was examined. The kinetics of Ca++ mobilization was observed using the dye fluo-3AM which is a membrane permeable Ca++ indicator which becomes increasingly fluorescent upon Ca++ binding. A baseline reading indicates the resting state of Ca++, followed by injection of Taurox-SB to yield final concentrations of 0.14 mM to 1.4 mM. The Taurox-SB-induced Ca++ mobilization appeared to be rising or sustained over the eight minute time period in which samples were run. PHA was added as a positive control for the elicitation of a Ca++ response (Greimers et al., 1996). The response decreased upon addition of EGTA to extracellular fluid chich indicates that the Ca++ response was both intracellular and extracellular in nature. (Data not shown.) The role of the second messenger response could be varied, as many proteins are activated by Ca++-regulated intracellular pathways. Second messengers may serve to enhance production of cytokines by immune cells.

Experiment 12

Taurox-SB Increases Human PBMC Proliferation

Treatment with 0.14 mM Taurox-SB increased proliferation of human PBMCs with and without PHA, as detected by incorporation of 3H-thymidine (Table 18). At a higher concentration of 1.4 mM a slight reduction in viability was observed, however lower concentrations were without significant effect. These results are consistent with elevated CD69 expression by Taurox-SB, indicating increased T cell activation. Further, cell cycle analysis performed at 18 and 24 hours of exposure to Taurox-SB showed an increase in the proportion of cells in G2/M. Representative data from one of 3 replicate experiments is set forth in Table 17.

TABLE 17

Taurox-SB treatment Increases PBMC Proliferation.*

| Treatment | No PHA | PHA |
| --- | --- | --- |
| Media | 1468 ± 205 | 4289 ± 984 |
| .014 mM Taurox-SB | 1346 ± 70 | 4794 ± 652 |
| 0.14 mM Taurox-SB | 2964 ± 684* | 5538 ± 597* |

Representative data from one of 3 replicate experiments. PHA was used at 10 μg/ml. Each condition was assayed in triplicate. Results are expressed as mean cpm ± SD. A "*" indicates significant at p < 0.1 relative to the media control.

Methods and Materials for the Proliferation Assays

Human PBMCs are obtained through collection of peripheral blood and isolation over Ficoll 1077. The cells are counted and 5×10$^5$ cells are plated in triplicate in 96 well plates in 100 μl of media (RPMI 1640, 20% FBS) containing specified conditions. These cells are then allowed to incubate for 48 hours. After this incubation 1 μCi of $^3$H-Thymidine is added in a 10 ml volume. The plates are incubated an additional 24 hours and harvested on a Tomtec plate harvester and the filtermat read in a scintillation counter. Many studies have been performed using the drugs in combination with PHA (T cell stimulant (mitogen)) obtained from Sigma.

All documents cited above are hereby incorporated in their entirety by reference. The entire contents of U.S. Provisional Application Nos. 60/005,336, filed Oct. 17, 1995; 60/075,966 and 60/085,474 are incorporated herein by reference.

One skilled in the art will appreciate from a reading of this disclosure that various changes in form and detail can be made without departing from the true scope of the invention.

What is claimed is:

1. A method of reducing soluble TNF alpha in an animal, comprising administering to the animal beta-alethine and N-acetyl-cysteine (NAC) in an amount sufficient to reduce soluble TNF alpha.

2. A method of treating a disease associated with elevated soluble TNF alpha levels in an animal, comprising administering to the animal an amount of beta-alethine and N-acetyl-cysteine (NAC) sufficient to treat the disease.

3. The method of claim 2, wherein the disease is one taken from the group comprising: anaphylactic shock or rheumatoid arthritis, systemic lupus erythematous (SLE), thyroiditis, diabetes, fibromyalgia or a collagen vascular disease.

4. A method of preventing or treating ischemia or reperfusion injury in an animal, comprising administering to the animal in need thereof a compound of Formula I or pharmaceutically acceptable salt thereof or physiologically hydrolysable derivative thereof (I)

wherein:

A is a group of the formula —PO$_3$H, —SO$_3$H, —OPO—(OH)$_2$ —OSO$_2$OH, or —SH, or pharmaceutically acceptable salt thereof or physiologically hydrolyzable derivative thereof, or disulfide thereof when A is —SH, R$_1$ is H, a linear or branched lower alkyl, an arylalkyl or an alkenyl,

R$_2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl, or R$^1$ and R$^2$ taken together form, with the nitrogen to which they are attached, a 5 to 7 membered ring, and L$^1$ and L$^2$ are, independently, a hydrocarbon linking group, a cycloalkyl, or an interphenylene, or pharmaceutically acceptable salt thereof, unionized form thereof or disulfide thereof, in an amount sufficient to prevent or treat ischemia or reperfusion injury.

5. A method of increasing production of cytotoxic T Lymphocytes in an animal, comprising administering to the animal an amount of a compound of Formula I sufficient to increase said production, wherein Formula I is:

(I)

wherein:

A is a group of the formula —PO$_3$H, —SO$_3$H, —OPO—(OH)$_2$, —OSO$_2$OH, or —SH, or pharmaceutically acceptable salt thereof or physiologically hydrolyzable derivative thereof, or disulfide thereof when A is —SH, R$_1$ is H, a linear or branched lower alkyl, an arylalkyl or an alkenyl, R$_2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl, or R$^1$ and R$^2$ taken together form, with the nitrogen to which they are attached, a 5 to 7 membered ring, and L$^1$ and L$^2$ are, independently, a hydrocarbon linking group, a cycloalkyl, or an interphenylene, or pharmaceutically acceptable salt thereof, unionized form thereof or disulfide thereof.

6. The method of claim 4 or claim 5, wherein

A is a group of the formula —PO$_3$H, —SO$_3$H, —OPO—(OH)$_2$, —OSO$_2$OH, or —SH, or pharmaceutically acceptable salt thereof or physiologically hydrolyzable (C$_1$–C$_4$)alkyl or arylalkyl ester thereof, or disulfide thereof when A is —SH;

R$_1$ is H, a linear or branched (C$_1$ to C$_6$)alkyl, a substituted or unsubstituted phenyl(C$_1$–C$_4$)alkyl, or a (C$_2$–C$_6$) alkenyl;

R$_2$ is H, a linear or branched (C$_1$ to C$_6$)alkyl, a (C$_2$–C$_6$) alkenyl, a substituted or unsubstituted phenyl (C$_1$–C$_4$) alkyl, an acetyl, benzoyl or arylsulfonyl, a (C$_1$–C$_7$) alkoxycarbonyl, —OCOCH$_2$CH=CH$_2$, a (C$_3$–C8) cyclo(C$_1$–C$_8$)alkoxycarbonyl, —OCOCH$_2$C$_6$H$_5$ or a substituted arylalkoxycarbonyl wherein the substituent is a halogen, a nitro group, an amino group or a methoxyl group;

or R$^1$ and R$^2$ taken together form, with the nitrogen to which they are attached, a 5 to 7 membered ring; and L$^1$ and L$^2$ are, independently, a linear or branched chain alkyl of the formula —(C$_n$H$_{2n}$)— wherein n is 1 to 8; a cycloalkyl of 3 to 8 carbon atoms, or an interphenylene, or pharmaceutically acceptable salt thereof or unionized form thereof, or disulfide thereof.

7. A method of increasing proliferation of T cells in an animal, comprising administering an amount of carbobenzoxy-beta-alanyl taurine sufficient to increase said proliferation.

8. A pharmaceutical composition comprising beta-alethine and N-acetyl-cysteine (NAC).

* * * * *